(12) United States Patent
Oka

(10) Patent No.: US 6,645,156 B2
(45) Date of Patent: Nov. 11, 2003

(54) CONTINUOUS BLOOD-PRESSURE MONITORING APPARATUS

(75) Inventor: Tohru Oka, Ichinomiya (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/985,408

(22) Filed: Nov. 2, 2001

(65) Prior Publication Data

US 2002/0138010 A1 Sep. 26, 2002

(30) Foreign Application Priority Data

Mar. 21, 2001 (JP) ........................... 2001-080625

(51) Int. Cl.[7] ................................................. A61B 5/02
(52) U.S. Cl. ........................ 600/490; 600/490; 600/500
(58) Field of Search ................................. 600/490, 493, 600/494, 495, 496, 500, 485, 481

(56) References Cited

U.S. PATENT DOCUMENTS

| 5,139,026 | A | | 8/1992 | Niwa | |
| 5,752,920 | A | * | 5/1998 | Ogura et al. | 600/494 |
| 5,860,932 | A | | 1/1999 | Goto et al. | |
| 5,921,936 | A | * | 7/1999 | Inukai et al. | 600/490 |
| 6,186,954 | B1 | * | 2/2001 | Narimatsu | 600/490 |
| 6,190,325 | B1 | * | 2/2001 | Narimatsu | 600/490 |
| 6,428,481 | B1 | * | 8/2002 | Inukai et al. | 600/485 |

FOREIGN PATENT DOCUMENTS

| EP | 0 885 589 A1 | 12/1998 |
| EP | 0 993 803 A1 | 4/2000 |

* cited by examiner

*Primary Examiner*—Max F. Hindenburg
*Assistant Examiner*—Navin Natnithithadha
(74) *Attorney, Agent, or Firm*—Oliff & Berridge, PLC

(57) ABSTRACT

A continuous blood-pressure monitoring device apparatus including a cuff, a first determining device, a detecting device which detects a pressure pulse wave produced by an artery, a second determining device, a monitoring device, an information obtaining device a first change-value determining device, a second change-value determining device, and a relationship checking device.

7 Claims, 11 Drawing Sheets

CONTINUOUS BLOOD-PRESSURE MONITORING APPARATUS

BACKGROUND OF THE INVENTION

1. Field of the Invention

The present invention relates to a continuous blood-pressure monitoring apparatus which includes a pressure-pulse-wave sensor adapted to be pressed against an artery of a living subject via the skin and continuously monitors blood pressure of the subject based on a pressure pulse wave detected by the sensor.

2. Related Art Statement

There is known a continuous blood-pressure monitoring apparatus which includes an inflatable cuff adapted to be worn on a portion of a living subject; a blood-pressure determining means for determining a blood pressure of the subject based on a signal obtained while a pressure in the cuff is slowly changed; a pressure-pulse-wave detecting device which includes a pressure-pulse-wave sensor adapted to be pressed against an artery of a prescribed portion of the subject and continuously detects a pressure pulse wave produced by the artery; a relationship determining means for determining, in advance, a relationship between blood pressure and magnitude of pressure pulse wave, based on the blood pressure determined by the blood-pressure determining means and a magnitude of the pressure pulse wave detected by the pressure-pulse-wave detecting device; and a blood-pressure monitoring means for successively determining, according to the thus determined relationship, a blood-pressure value of the subject based on each of respective magnitudes of the pressure pulse wave detected by the pressure-pulse-wave detecting device. Since the blood-pressure values successively determined by the continuous blood-pressure monitoring apparatus are very highly reliable, the apparatus can be used in those cases in which strict blood-pressure monitoring is needed. This apparatus is disclosed in, e.g., Japanese Utility Model Document No. 2-82309 or its corresponding U.S. Pat. No. 5,139,026.

In the continuous blood-pressure monitoring apparatus, disclosed in the above-indicated document, in which the pressure-pulse-wave sensor is pressed against an artery of a prescribed portion of a living subject, a condition under which the sensor is pressed against the artery may be changed by, e.g., a change of a state in which the sensor is worn, caused by a physical motion of the subject. Hence, in order to increase the reliability of blood-pressure values determined by the blood-pressure monitoring means, a calibration is periodically carried out to update the relationship between blood pressure and magnitude of pressure pulse wave. In each calibration, the blood-pressure determining means determines a new blood pressure of the subject in a process in which the pressure of the cuff is changed in a prescribed manner, and the relationship determining means determines a new relationship between blood pressure and magnitude of pressure pulse wave, based on the new blood pressure determined by the blood-pressure determining means and a magnitude of the pressure pulse wave detected by the pressure-pulse-wave sensor during the above-indicated process.

However, when each calibration is carried out, the cuff is inflated to press the subject's portion, thereby causing the subject to feel discomfort. In addition, the calibration is periodically carried out irrespective of whether the condition under which the sensor is pressed is appropriate or not, and the calibration period needs to be shortened to increase the reliability of continuous monitoring of blood pressure. Thus, the burden exerted on the subject is increased.

In order to solve the above-indicated problem, Japanese Patent Document No. 7-284479 or its corresponding U.S. Pat. No. 5,860,932 discloses a continuous blood-pressure monitoring apparatus in which a pressure-pulse-wave sensor is worn on a portion of a subject that is located on a downstream side of a cuff, a pressure of the cuff is increased at a prescribed rate, and a judging means judges whether a relationship between blood pressure and pressure-pulse-wave magnitude is appropriate, based on a shape or an area of a pressure pulse wave detected by the sensor during the increasing of the cuff pressure. More specifically described, the disclosed apparatus determines, in a state in which the cuff pressure would be substantially equal to, or somewhat higher than, a diastolic blood pressure of the subject, the diastolic blood pressure of the subject by utilizing the fact that the tendency of change of respective shapes or areas of respective heartbeat-synchronous pulses of the pressure pulse wave, successively detected by the sensor during the increasing of the cuff pressure, significantly changes around the diastolic blood pressure, compares the thus determined diastolic blood pressure with a diastolic blood pressure determined based on a magnitude of a heartbeat-synchronous pulse of the pressure pulse wave according to the relationship between blood pressure and pressure-pulse-wave magnitude, and judges whether the relationship is appropriate. If it is judged that the relationship is appropriate, then it is not needed to carry out a calibration, which leads to reducing the discomfort the subject suffers.

However, even in the above-described continuous blood-pressure monitoring apparatus, the cuff pressure is increased up to a value substantially equal to, or somewhat higher than, the diastolic blood pressure, so as to judge whether the relationship is appropriate or not. Thus, the discomfort the subject suffers is not sufficiently reduced.

In addition, in the above-described continuous blood-pressure monitoring apparatus, the pressure-pulse-wave sensor needs to be worn on the subject's portion located on the downstream side of the cuff. On the other hand, in many cases, the continuous blood-pressure monitoring apparatus is used during a surgical operation or in an intensive care unit when or where many devices are connected to the subject and, in some cases, the pressure-pulse-wave sensor cannot be worn on the subject's portion located on the downstream side of the cuff.

SUMMARY OF THE INVENTION

It is therefore an object of the present invention to provide a continuous blood-pressure monitoring apparatus which sufficiently reduces discomfort felt by a living subject and sufficiently increases freedom of wearing.

The above object has been achieved by the present invention. According to a first aspect of the present invention, there is provided an apparatus for continuously monitoring a blood pressure of a living subject, comprising an inflatable cuff which is adapted to be wound around a portion of the subject, a cuff pulse wave including a plurality of heartbeat-synchronous pulses occurring to the cuff while a pressure in the cuff is changed; a blood-pressure determining means for determining a blood pressure of the subject based on a signal obtained while the pressure of the cuff is changed; a pressure-pulse-wave detecting device which includes a pressure-pulse-wave sensor that is adapted to be pressed against an artery of the subject and which continuously detects, through the pressure-pulse-wave sensor, a pressure pulse wave that is produced by the artery and includes a plurality of heartbeat-synchronous pulses; a relationship determining means for determining a relationship between blood pressure and magnitude of pressure pulse wave, based on the blood pressure determined by the blood-pressure determining means and a magnitude of the pressure pulse wave detected by the pressure-pulse-wave detecting device; a blood-pressure monitoring means for iteratively determining, according to the thus determined relationship, a monitor blood-pressure value of the subject based on a magnitude of each of the heartbeat-synchronous pulses of the pressure pulse wave detected by the pressure-pulse-wave detecting device; a pulse-wave-propagation-velocity-related-information obtaining means for iteratively obtaining, in a state in which the pressure of the cuff is held at a prescribed pulse-wave-detection pressure lower than a diastolic blood pressure of the subject, a piece of pulse-wave-propagation-velocity-related information which is related to a velocity at which a pulse wave propagates through the artery of the subject, based on a time of occurrence of a prescribed periodic point of a heartbeat-synchronous pulse of the cuff pulse wave and a time of occurrence of a prescribed periodic point of a corresponding heartbeat-synchronous pulse of the pressure pulse wave; a propagation-velocity-related-information-change-value determining means for periodically determining, at a prescribed judgment period, a change value of the pieces of pulse-wave-propagation-velocity-related information obtained by the pulse-wave-propagation-velocity-related-information obtaining means; a monitor-blood-pressure-change-value determining means for periodically determining, at the judgment period, a change value of the monitor blood-pressure values determined by the blood-pressure monitoring means; and a relationship checking means for comparing the change value of the pieces of pulse-wave-propagation-velocity-related information, determined by the propagation-velocity-related-information-change-value determining means, and the change value of the monitor blood-pressure values, determined by the monitor-blood-pressure-change-value determining means, with each other, and thereby judging whether the relationship between blood pressure and magnitude of pressure pulse wave, determined by the relationship determining means, is appropriate.

According to this aspect, the pulse-wave-propagation-velocity-related-information obtaining means obtains the piece of pulse-wave-propagation-velocity-related information, between the cuff and the pressure-pulse-wave detecting device, and the propagation-velocity-related-information-change-value determining means determines, at the judgment period, the change value of the piece of pulse-wave-propagation-velocity-related information. Since the pulse-wave-propagation-velocity-related information changes with the change of blood pressure of the subject, the change value of the piece of pulse-wave-propagation-velocity-related information corresponds to the amount of change of blood pressure. In addition, the change value of the monitor blood-pressure value determined by the monitor-blood-pressure-change-value determining means also corresponds to the amount of change of blood pressure. However, when the condition under which the pressure-pulse-wave detecting device is worn on the subject has changed and the monitor blood-pressure value determined by the blood-pressure monitoring means is not accurate, the change value of the monitor blood-pressure value largely differs from the change value of the piece of pulse-wave-propagation-velocity-related information. Therefore, the relationship checking means compares the change value of the monitor blood-pressure value and the change value of the piece of pulse-wave-propagation-velocity-related information, with each other, and judges whether the relationship between blood pressure and pressure pulse wave, determined by the relationship determining means, is appropriate.

Therefore, a longer period can be employed to operate the blood-pressure determining means and thereby update the relationship between blood pressure and pressure pulse wave, and accordingly the discomfort the subject feels can be reduced. In addition, since the pulse-wave-propagation-velocity-related information is obtained based on the cuff pulse wave detected in the state in which the pressure of the cuff is held at the prescribed pulse-wave-detection pressure lower than the diastolic blood pressure of the subject, the subject feels minimized discomfort only. Moreover, since the pulse-wave-propagation-velocity-related information can be determined even if the pressure-pulse-wave detecting device may not be worn on the downstream side of the cuff, the detecting device can be worn on the other arm than the arm around which the cuff is wound.

According to a second aspect of the present invention, there is provided an apparatus for continuously monitoring a blood pressure of a living subject, comprising an inflatable cuff which is adapted to be wound around a portion of the subject, a cuff pulse wave including a plurality of heartbeat-synchronous pulses occurring to the cuff while a pressure in the cuff is changed, a blood-pressure determining means for determining a blood pressure of the subject based on a signal obtained while the pressure of the cuff is changed; a pressure-pulse-wave detecting device which includes a pressure-pulse-wave sensor that is adapted to be pressed against an artery of the subject and which continuously detects, through the pressure-pulse-wave sensor, a pressure pulse wave that is produced by the artery and includes a plurality of heartbeat-synchronous pulses; a first relationship determining means for determining a first relationship between blood pressure and magnitude of pressure pulse wave, based on the blood pressure determined by the blood-pressure determining means and a magnitude of the pressure pulse wave detected by the pressure* pulse-wave detecting device; a blood-pressure monitoring means for successively determining, according to the thus determined first relationship, a monitor blood-pressure value of the subject based on a magnitude of each of the heartbeat-synchronous pulses of the pressure pulse wave detected by the pressure-pulse-wave detecting device; a standard-pulse-wave-propagation-velocity-related-information obtaining means for obtaining, as a standard piece of pulse-wave-propagation-velocity-related information, a piece of pulse-wave-propagation-velocity-related information which is related to a velocity at which a pulse wave propagates through the artery of the subject, based on a time of occurrence of a prescribed periodic point of a heartbeat-synchronous pulse of the cuff pulse wave in a first time duration comprising at least one of a first time period in which the pressure of the cuff is changed, a prescribed preceding time period preceding the first time period, and a prescribed following time period following the first time period, and a time of occurrence of a prescribed periodic point of a corresponding heartbeat-synchronous pulse of the pressure pulse wave in the first time duration; a second relationship determining means for determining a second relationship between blood pressure and pulse-wave-propagation-velocity-related information, based on the blood pressure determined by the blood-pressure determining means and the standard piece of pulse-wave-propagation-velocity-related information obtained by the standard-pulse-wave-propagation-velocity-related-information obtaining means; a cuff-pressure changing means for periodically increasing, at a prescribed judgment period, the pressure of the cuff up to a prescribed pulse-wave-detection pressure lower than a diastolic blood pressure of the subject; a judgment-pulse-wave-propagation-velocity-related information obtaining means for obtaining, as a judgment piece of pulse-wave-propagation-velocity-related information, a piece of pulse-wave-propagation-velocity-related information which is related to the velocity at which the pulse wave propagates through the artery of the subject, based on a time of occurrence of a prescribed periodic point of a heartbeat-synchronous pulse of the cuff pulse wave occurring to the cuff in a state in which the pressure of the cuff is held at the pulse-wave-detection pressure by the cuff-pressure changing means, and a time of occurrence of a prescribed periodic point of a corresponding heartbeat-synchronous pulse of the pressure pulse wave detected by the pressure-pulse-wave detecting device in the state; an estimated-blood-pressure determining means for determining, according to the second relationship, an estimated blood-pressure value of the subject based on the judgment piece of pulse-wave-propagation-velocity-related information obtained by the judgment-pulse-wave-propagation-velocity-related-information obtaining means; and a relationship checking means for comparing the estimated blood-pressure value determined by the estimated-blood-pressure determining means, and a monitor blood-pressure value determined by the blood-pressure monitoring means based on a magnitude of a heartbeat-synchronous pulse of the pressure pulse wave detected by the pressure-pulse-wave detecting device in a second time duration comprising at least one of a second time period in which the pressure of the cuff is held at the pulse-wave-detection pressure by the cuff-pressure changing means, a prescribed preceding time period preceding the second time period, and a prescribed following time period following the second time period, with each other, and thereby judging whether the relationship between blood pressure and magnitude of pressure pulse wave, determined by the relationship determining means, is appropriate.

According to this aspect, the estimated-blood-pressure determining means determines the estimated blood-pressure value based on the judgment-pulse-wave-propagation-velocity-related information according to the relationship between blood pressure and pulse-wave-propagation-velocity-related information. If the condition under which the pressure-pulse-wave detecting device is worn on the subject has changed and accordingly the monitor blood-pressure value determined by the blood-pressure monitoring means is not accurate, the monitor blood-pressure value largely differs from the estimated blood-pressure value. Hence, the relationship checking means compares the estimated blood-pressure value and the monitor blood-pressure value determined based on the pressure pulse wave by the blood-pressure monitoring means, with each other, and judges whether the relationship between blood pressure and pressure pulse wave, determined by the first relationship determining means, is appropriate or not.

Therefore, a longer period can be employed to operate the blood-pressure determining means and thereby update the relationship between blood pressure and pressure pulse wave, and accordingly the discomfort the subject feels can be reduced. In addition, since the judgment-pulse-wave-propagation-velocity-related information is obtained based on the cuff pulse wave detected in the state in which the pressure of the cuff is held by the cuff-pressure changing means at the value sufficiently lower than the diastolic blood pressure of the subject, the subject feels minimized discomfort only. Moreover, since the standard-pulse-wave-propagation-velocity-related information used to determine the relationship between blood pressure and pulse-wave-propagation-velocity-related information, and the judgment-pulse-wave-propagation-velocity-related information used to determine the estimated blood-pressure value can each be determined even if the pressure-pulse-wave detecting device may not be worn on the downstream side of the cuff, the detecting device can be worn on the other arm than the arm around which the cuff is wound.

According to a preferred feature of the first aspect of the invention, the relationship checking means judges that the relationship between blood pressure and magnitude of pressure pulse wave is not appropriate, when a relative value between the change value of the pieces of pulse-wave-propagation-velocity-related information, determined by the propagation-velocity-related-information-change-value determining means, and the change value of the monitor blood-pressure values, determined by the monitor-blood-pressure-change-value determining means, does not fall within a normal range, and the apparatus further comprises a normal-range determining means for determining, as the normal range, a narrower range when the monitor blood-pressure value used to determine the change value of the monitor blood-pressure values is lower than a prescribed danger value which indicates that the subject needs an urgent treatment, than a range determined thereby when the monitor blood-pressure value is not lower than the danger value.

According to this feature, when the monitor blood-pressure value is lower than the prescribed danger value, whether the relationship is appropriate or not is more strictly checked. Therefore, the accuracy of the monitor blood-pressure value determined when the blood pressure of the subject is low is improved, and whether the blood pressure of the subject is so low as to need an urgent treatment can be judged quickly and reliably.

According to a preferred feature of the second aspect of the invention, the relationship checking means judges that the relationship between blood pressure and magnitude of pressure pulse wave is not appropriate, when a relative value between the estimated blood-pressure value determined by the estimated-blood-pressure determining means, and a monitor blood-pressure value determined by the blood-pressure monitoring means based on a magnitude of a heartbeat-synchronous pulse of the pressure pulse wave detected by the pressure-pulse-wave detecting device in the second time period in which the pressure of the cuff is held at the pulse-wave-detection pressure by the cuff-pressure changing means, does not fall within a normal range, and the apparatus further comprises a normal-range determining means for determining, as the normal range, a narrower range when at least one of the estimated blood-pressure value and the monitor blood-pressure value is lower than a prescribed danger value which indicates that the subject needs an urgent treatment, than a range determined thereby when each of the estimated blood-pressure value and the monitor blood-pressure value is not lower than the danger value.

According to this feature, when at least one of the estimated blood-pressure value and the monitor blood-pressure value is lower than the prescribed danger value, whether the first relationship is appropriate or not is more strictly checked. Therefore, the accuracy of the monitor blood-pressure value determined when the blood pressure of the subject is low is improved, and whether the blood pressure of the subject is so low as to need an urgent treatment can be judged quickly and reliably.

Preferably, the relationship checking means comprises means for operating, when it is judged that the relationship between blood pressure and magnitude of pressure pulse wave is not appropriate, the relationship determining means to update the relationship.

According to this feature, since the inappropriate relationship is quickly updated and corrected and the monitor blood-pressure values are determined according to the corrected relationship, the reliability of the monitor blood-pressure values is improved.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
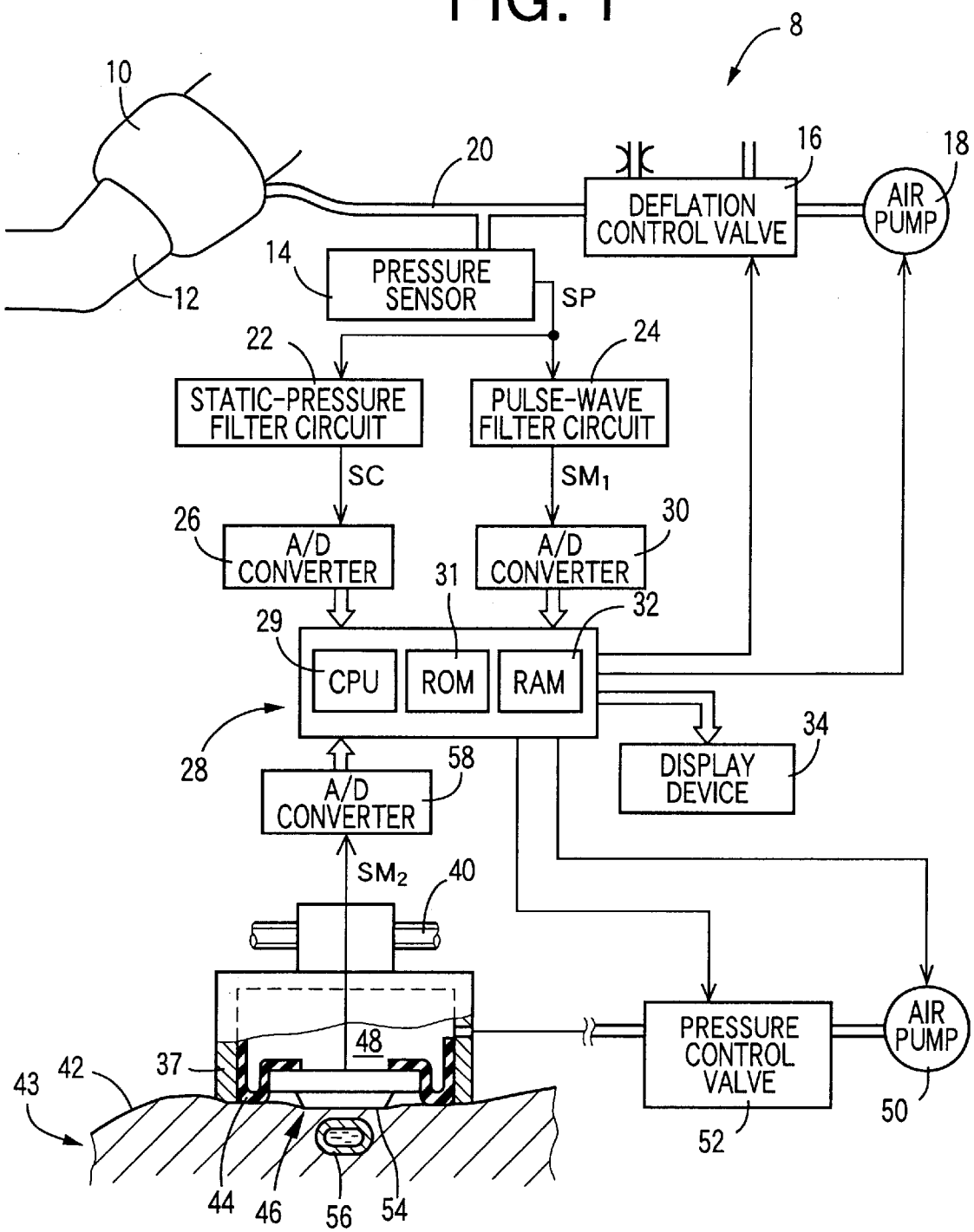
FIG. 1 is a diagrammatic view for explaining a construction of a continuous blood-pressure monitoring apparatus to which the present invention is applied.

Hereinafter, there will be described an embodiment of the present invention in detail by reference to the drawings. FIG. 1 shows a diagrammatic view for explaining a construction of a continuous blood-pressure monitoring apparatus 8 to which the present invention is applied.

In FIG. 1, reference numeral 10 designates an inflatable cuff which has a belt-like cloth bag and a rubber bag accommodated in the cloth bag and which is adapted to be wound around, e.g., a right upper arm 12 of a patient as a living subject. The cuff 10 is connected to a pressure sensor 14, a deflation control valve 16, and an air pump 18 via a piping 20. The deflation control valve 16 is selectively placed in a pressure-supply position in which the control valve 16 permits a pressurized air to be supplied from the air pump 18 to the cuff 10, a pressure-maintain position in which the control valve 16 maintains a pressure in the cuff 10; a slow-deflation position in which the control valve 16 permits the pressurized air to be slowly discharged from the cuff 10, and a quick-deflation position in which the control valve 16 permits the pressurized air to be quickly discharged from the cuff 10.

The pressure sensor 14 detects an air pressure Pc in the cuff 10, and supplies a pressure signal SP representing the detected pressure Pc, to each of a static-pressure filter circuit 22 and a pulse-wave filter circuit 24. The static-pressure filter circuit 22 includes a low-pass filter and extracts, from the pressure signal SP, a static-pressure component contained in the signal SP, i.e., a cuff-pressure signal SC representing the static pressure in the cuff 10. The cuff-pressure signal SC is supplied to a control device 28 via an analog-to-digital (A/D) converter 26. The pulse-wave filter circuit 24 includes a band-pass filter and extracts, from the pressure signal SP, an oscillating component having predetermined frequencies, i.e., a cuff-pulse-wave signal $SM_1$. The cuff-pulse-wave signal $SM_1$ is supplied to the control device 28 via an A/D converter 30. The cuff-pulse-wave signal $SM_1$ represents a cuff pulse wave KW, i.e., an oscillatory pressure wave which is produced from a brachial artery, not shown, of the patient in synchronism with the heartbeat of the patient and is propagated to the cuff 10.

The control device 28 is provided by a so-called microcomputer including a central processing unit (CPU) 29, a read only memory (ROM) 31, a random access memory (RAM) 32 and an input-and-output (I/O) port, not shown. The CPU 29 processes signals according to the control programs pre-stored in the ROM 31 by utilizing the temporary-storage function of the RAM 32, and supplies drive signals via the I/O port to respective drive circuits, not shown, associated with the deflation control valve 16 and the air pump 18 so as to control the air pressure in the cuff 10 and determine, according to oscillometric method, a blood-pressure value BP of the patient, such as a systolic blood-pressure value $BP_{SYS}$ and/or a diastolic blood-pressure value $BP_{DIA}$, based on change of the cuff pulse wave KW represented by the cuff-pulse-wave signal $SM_1$. In addition, the CPU 29 operates a display device 34 to display the thus determined blood-pressure value BP. The display device 32 may have a cathode ray tube (CRT).

Figure 2:
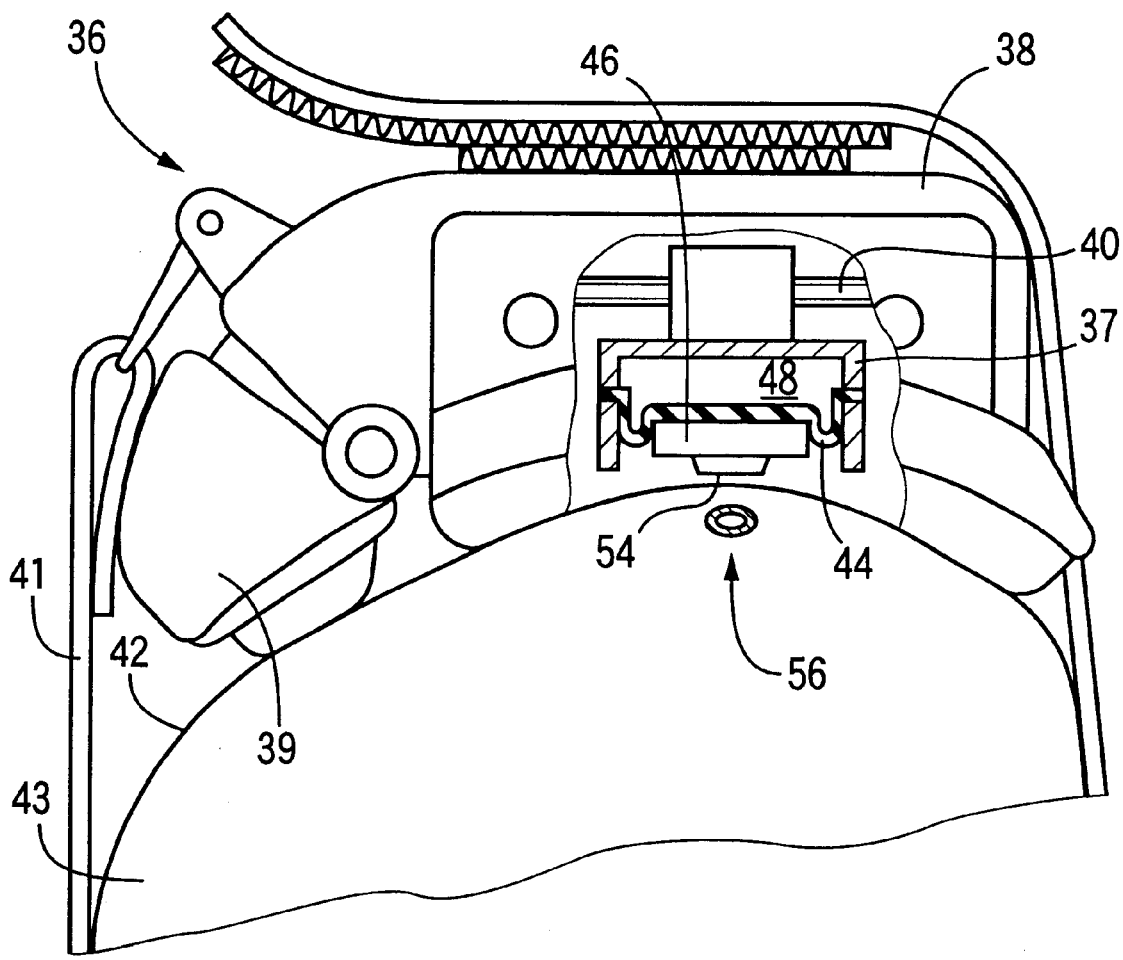
FIG. 2 is an enlarged view of a pressure-pulse-wave detecting probe of the apparatus of FIG. 1, a portion of the probe being cut away.

The monitoring apparatus 8 further includes a pressure-pulse-wave detecting probe 36 functioning as a pressure-pulse-wave detecting device. As shown in detail in FIG. 2, the pressure-pulse-wave detecting probe 36 includes a case 38 which accommodates a container-like sensor housing 37; and a feed screw 40 which is threadedly engaged with the sensor housing 37 and is rotated by an electric motor, not shown, provided in a drive section 39 of the case 38 so as to move the sensor housing 37 in a widthwise direction of a radial artery 56. With the help of a fastening band 41 which is connected to the case 38, the case 38 is detachably attached to a wrist 43 of the other arm (e.g., left arm) than the arm wound which the cuff 10 is wound, such that an open end of the sensor housing 37 is opposed to a body surface 42 of the wrist. In addition, the probe 36 includes a pressure-pulse-wave sensor 46 which is secured via a diaphragm 44 to an inner wall of the sensor housing 37, such that the sensor 46 is movable relative to the housing 37 and is advanceable out of the open end of the same 37. The sensor housing 37, the diaphragm 44, etc. cooperate with one another to define a pressure chamber 48, which is supplied with a pressurized air from an air pump 50 via a pressure-control valve 52 so that the pressure-pulse-wave sensor 46 is pressed against the body surface 42 with a pressing force $P_{HDP}$ corresponding to the air pressure in the pressure chamber 48. Thus, the pressing force $P_{HDP}$ applied to the sensor 46 is expressed in terms of the air pressure (mmHg) in the pressure chamber 48.

The sensor housing 37 and the diaphragm 44 cooperate with each other to provide a pressing device 62 which presses the pressure-pulse-wave sensor 46 against the radial artery 56, with an optimum pressing force $P_{HDPO}$, described later. The feed screw 40 and the not-shown motor cooperate with each other to provide a pressing-position changing device or a widthwise-direction moving device 64 which moves the pressure-pulse-wave sensor 46 in the widthwise direction of the radial artery 56 and thereby changes a pressing position where the sensor 46 is pressed.

The pressure-pulse-wave sensor 46 includes a semiconductor chip provided by, e.g., a monocrystalline silicon, and having a flat press surface 54, and a number of semiconductor pressure-sensing elements (not shown) arranged on the press surface 54 at a regular interval of about 0.2 mm in the widthwise direction of the radial artery 56 (i.e., the direction of movement of the sensor 46 parallel to the feed screw 40). The sensor 46 is pressed against the body surface 42 of the wrist 43 right above the radial artery 56, to detect a pressure pulse wave PW(t), i.e., an oscillatory pressure wave which is produced from the radial artery 56 and is propagated to the body surface 42, and supplies a pressure-pulse-wave signal $SM_2$ representing the pressure pulse wave PW(t), to the control device 28 via an A/D converter 58.

The CPU 29 of the control device 28 processes signals according to the control programs pre-stored in the ROM 31 by utilizing the temporary-storage function of the RAM 32, and supplies drive signals to respective drive circuits, not shown, associated with the pressure control valve 52 and the air pump 50 so as to control the air pressure in the pressure chamber 48. In addition, the control device 28 determines, based on the pressure pulse wave PW(t) continuously detected by the pressure-pulse-wave sensor 46 while the pressure in the pressure chamber 48 is slowly changed, an optimum pressing pressure $P_{HDPO}$ at which the sensor 46 is optimally pressed against the radial artery 56 such that a portion of the wall of the artery 56 is substantially flattened. The control device 28 controls the pressure control valve 52 so as to maintain the pressure of the pressure chamber 48 at the thus determined optimum pressing pressure $P_{HDPO}$.

Figure 3:
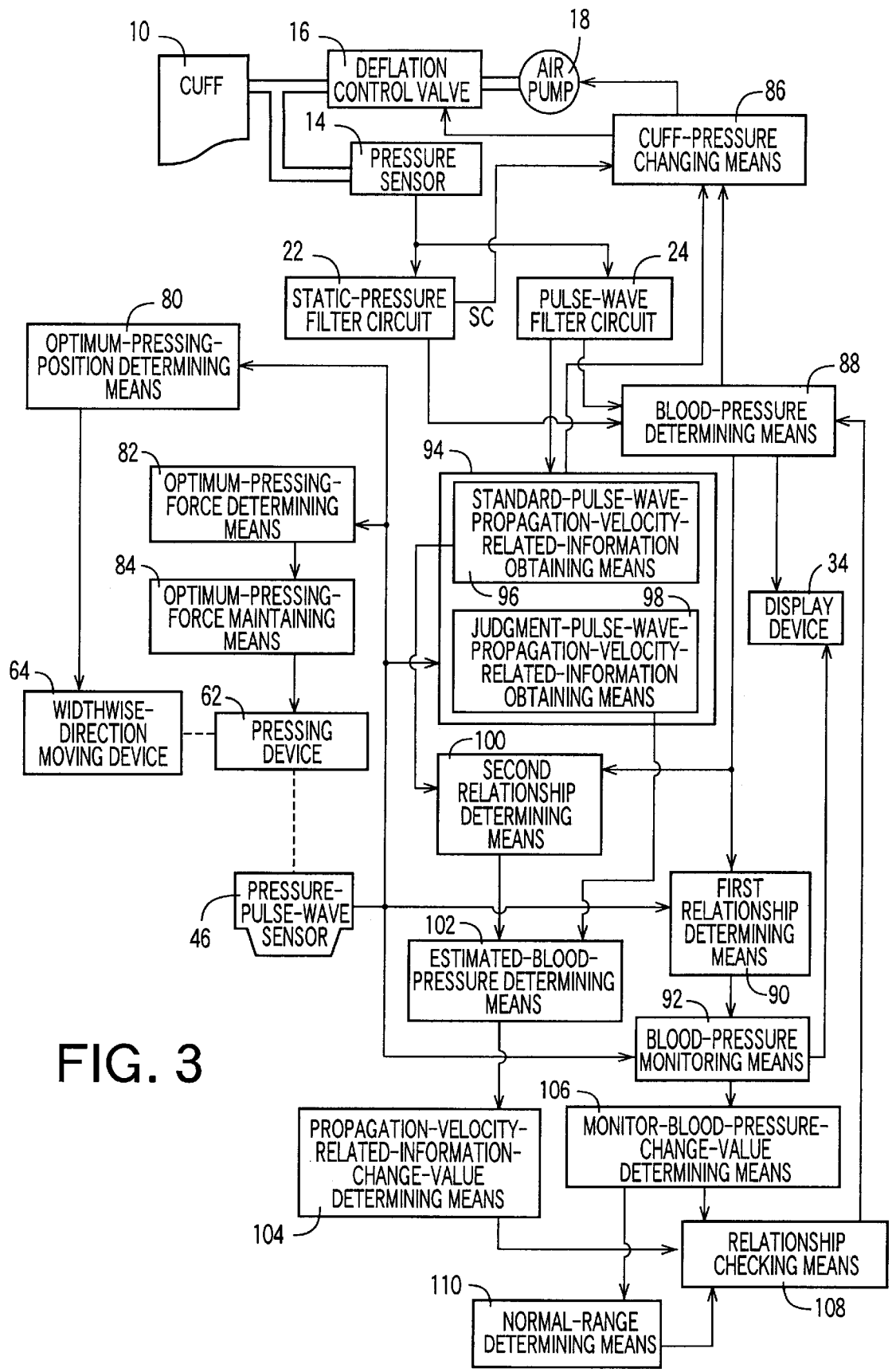
FIG. 3 is a block diagram for explaining essential functions of a control device of the apparatus of FIG. 1.

FIG. 3 is a block diagram for explaining essential functions of the control device 28. In the figure, an optimum-pressing-position determining means 80 operates when a prescribed pressing-position changing condition (i.e., an APS-starting condition) is satisfied, for example, when the pressure-pulse-wave detecting probe 36 is initially worn on the patient, or when the sensor 46 is largely moved relative to the radial artery 56 so that one of the pressure-sensing elements of the sensor 46 that detects the greatest one of the respective amplitudes of heartbeat-synchronous pulses detected by all the pressure-sensing elements is located in one of prescribed opposite end portions of the array of pressure-sensing elements. When the APS-starting condition is satisfied, first, the determining means 80 operates the pressing device 62 to press the pressure-pulse-wave sensor 46 at a first prescribed pressing pressure $P_1$ which would be sufficiently lower than an optimum pressing pressure $P_{HDPO}$ and, in this state, judges whether the one pressure-sensing element that detects the greatest amplitude is located in a prescribed middle range of the array of pressure-sensing elements. If a negative judgment is made, that is, if the one pressure-sensing element that detects the greatest amplitude is not positioned in the prescribed middle range, then the determining means 70 operates the pressing device 62 to move the sensor 46 away from the body surface 42 and operates the moving device 64, and again performs the above-described pressing and judging operations. Meanwhile, if a positive judgment is made indicating that the sensor 46 has been positioned at an optimum pressing position, the determining means 80 determines the pressure-sensing element detecting the greatest amplitude, as a middle pressure-sensing element (i.e., an active element), and stores data indicating the pressure-sensing element determined as the active element. Then, the determining means 80 allows an optimum-pressing-force determining means 82 to operate.

Figure 4:
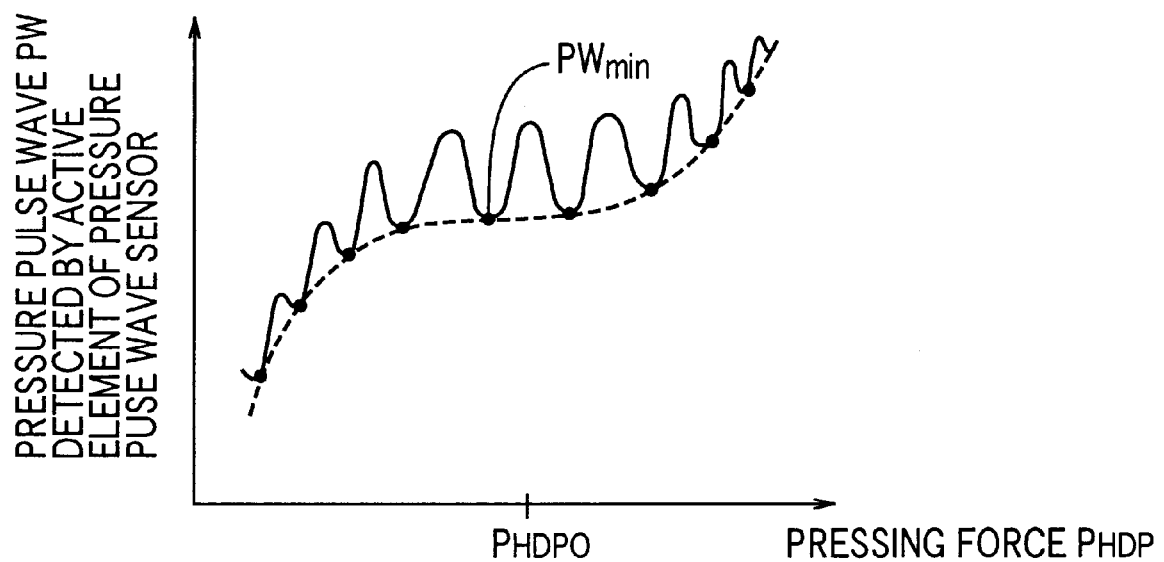
FIG. 4 is a graph for explaining a manner in which an optimum pressing force is determined by an optimum-pressing-force determining means shown in FIG. 3.

The optimum-pressing-force determining means 82 continuously changes the pressing pressure $P_{HDP}$ applied to the pressure-pulse-wave sensor 46 positioned at the optimum pressing position by the optimum-pressing-position determining means 80, and determines an optimum pressing pressure $P_{DHPO}$ based on the pressure pulse wave PW(t) detected by the active element of the sensor 46. The optimum pressing pressure $P_{DHPO}$ may be determined as follows: First, as shown in a two-dimensional graph shown in FIG. 4, respective minimal values $PW_{min}$ of respective heartbeat-synchronous pulses of the pressure pulse wave PW detected by the active element of the sensor 46 when the pressing pressure $P_{HDP}$ is continuously increased in a pressure range which would include the optimum pressing pressure $P_{DHPO}$, are determined, and then a curve (indicated at broken line in FIG. 4) connecting the respective minimal values $PW_{min}$ of the pressure pulse wave PW is determined. Further, the optimum pressing pressure $P_{DHPO}$ is determined as a pressure which falls within a pressure range which has a prescribed width and whose middle pressure is equal to a middle pressure of a pressure range in which the thus determined curve is substantially horizontal. If the radial artery 56 is pressed by the sensor 46 with the pressure falling within the latter pressure range, a portion of the wall of the artery 56 that is pressed by the sensor 46 is so deformed as to be substantially flat.

Figure 5:
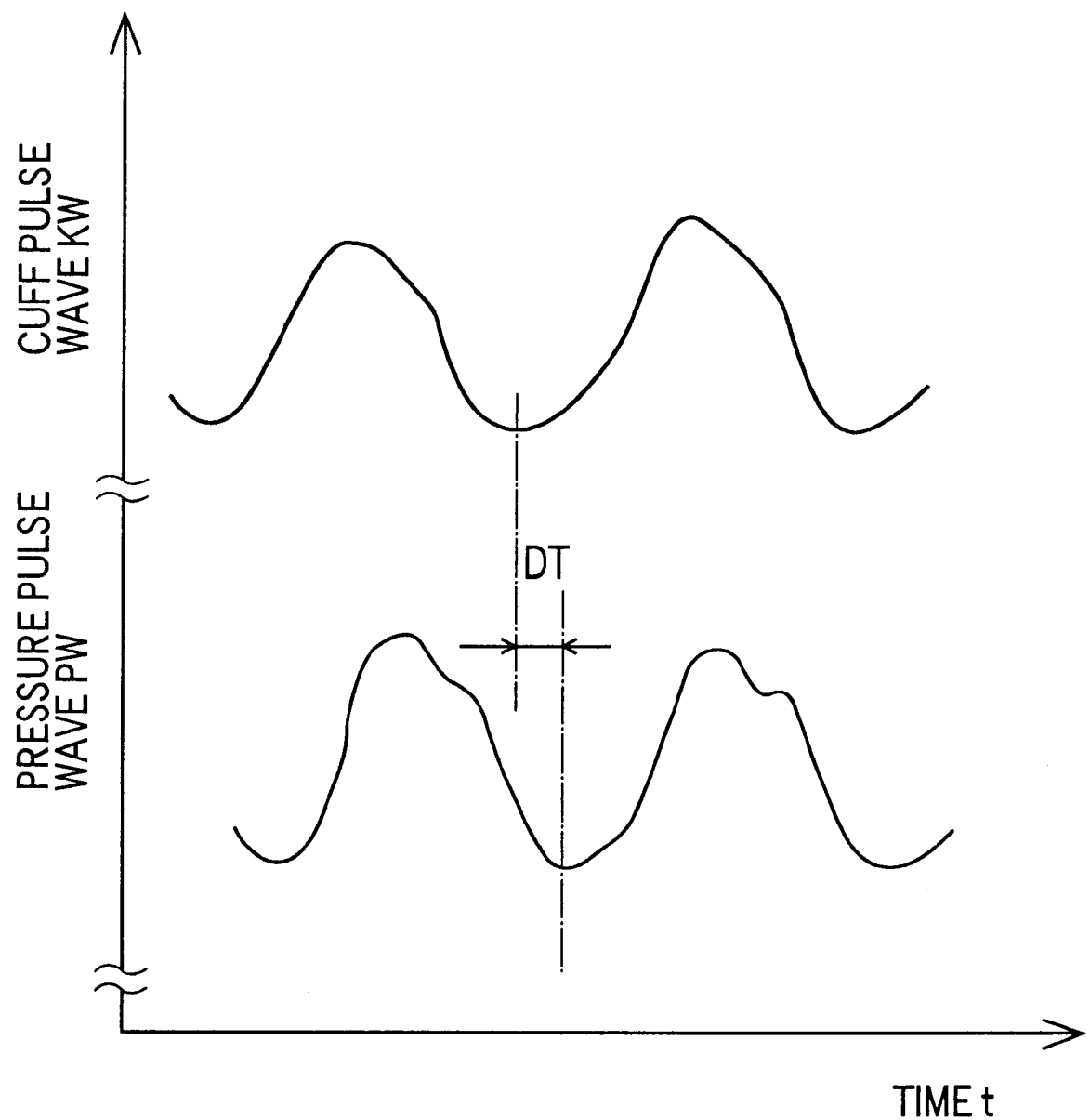
FIG. 5 is a graph showing respective examples of a pressure pulse wave PW(t) continuously detected by a pressure-pulse-wave sensor in a state in which a pressing force $P_{HDP}$ applied to the pressure-pulse-wave sensor is held at the optimum pressing force $P_{HDPO}$, and a cuff pulse wave KW detected in a state in which a pressure in an inflatable cuff is held at a pulse-wave-detection pressure $P_{CM2}$.

An optimum-pressing-force maintaining means 84 operates the air pump 50 and the pressure control valve 52 to maintain the pressing pressure $P_{HDP}$ applied by the pressing device 62 to the pressure-pulse-wave sensor 46, at the optimum pressing pressure $P_{HDPO}$ determined by the optimum-pressing-force determining means 82. FIG. 5 shows two heartbeat-synchronous pulses of a pressure pulse wave PW(t) which are successively detected by the active element of the pressure-pulse-wave sensor 46 in the state in which the pressing pressure $P_{HDP}$ applied to the sensor 46 is maintained at the optimum pressing pressure $P_{HDPO}$.

A cuff-pressure changing means 86 operates the air pump 18 and the deflation control valve 16, in response to a command signal supplied from a blood-pressure determining means 88 or a judgment-pulse-wave-propagationvelocity-related-information obtaining means 98, each described later, and based on the cuff-pressure signal SC supplied from the static-pressure filter circuit 22. In response to the command signal supplied from the blood-pressure determining means 88, the changing means 86 operates the air pump 18 and the control valve 16 to quickly increase the pressure of the cuff 10, i.e., the cuff pressure Pc up to a prescribed target pressure $P_{CM1}$ (e.g., 180 mmHg) which would be higher than a systolic blood-pressure value $BP_{SYS}$ of the patient and subsequently slowly decrease the cuff pressure Pc at a rate of from 2 to 3 mmHg/sec. After the blood-pressure determining means 88 determines a blood pressure BP of the patient, the changing means 86 quickly decreases the cuff pressure Pc down to an atmospheric pressure. Meanwhile, in response to the command signal supplied from the judgment-pulse-wave-propagation-velocity-related-information obtaining means 98, the changing means 86 operates the air pump 18 and the control valve 16 to the cuff pressure Pc up to a prescribed pulse-wave-detection pressure $P_{CM2}$ (e.g., 30 mmHg) and subsequently maintain the cuff pressure Pc at the pressure $P_{CM2}$ for a prescribed time duration which would correspond to two or three heartbeats of the patient. The pulse-wave-detection pressure $P_{CM2}$ is a pressure which is sufficiently lower than a common diastolic blood pressure and which assures that an oscillatory pressure wave produced by a brachial artery is transmitted to the cuff 10 and a cuff pulse wave WK representing the oscillatory pressure wave is detected with a sufficiently great signal magnitude from the cuff 10. FIG. 5 shows two heartbeat-synchronous pulses of a cuff pulse wave KW detected by the pulse-wave filter circuit 24 in the state in which the pressure of the cuff 10 is maintained at the pulse-wave-detection pressure $P_{CM2}$.

A blood-pressure determining means 88 determines a systolic blood-pressure value $BP_{SYS}$, a mean blood-pressure value $BP_{MEAN}$, and a diastolic blood-pressure value $BP_{DIA}$ of the patient, based on the change of the cuff-pulse-wave signal $SM_1$ obtained while the pressure of the cuff 10 is slowly decreased by the cuff-pressure changing means 86, according to well-known oscillometric method. In addition, the determining means 88 operates the display device 34 to display the thus determined blood-pressure values $BP_{SYS}$, etc.

Figure 6:
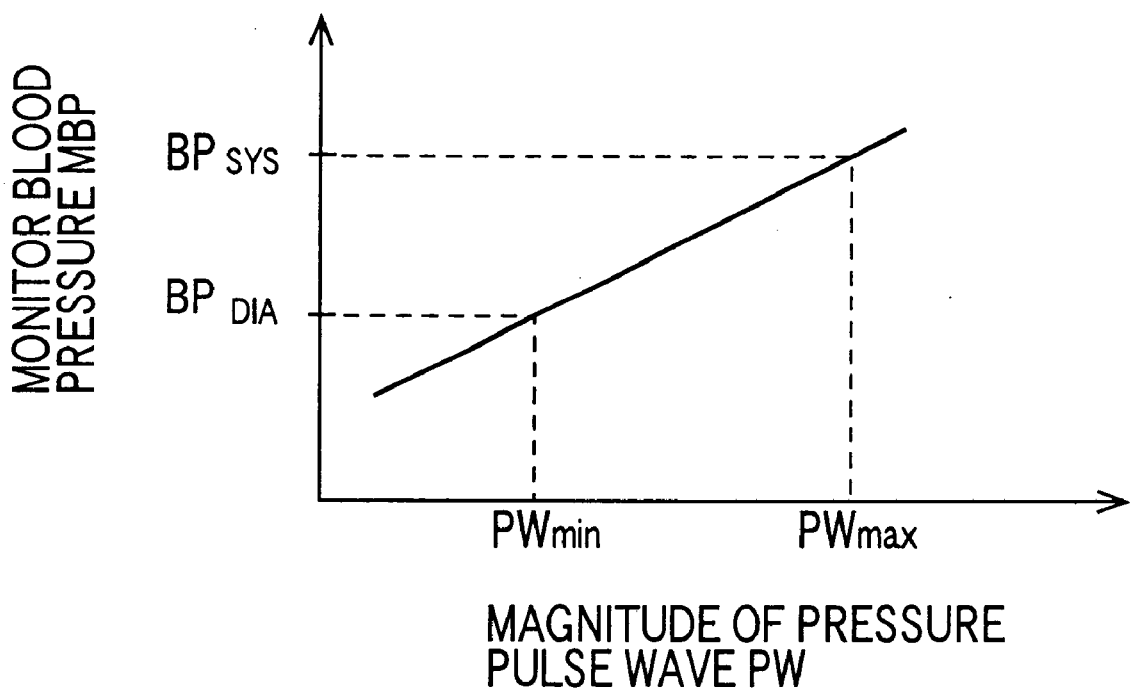
FIG. 6 is a graph showing an example of a relationship determined by a relationship determining means shown in FIG. 3.

A first relationship determining means 90 operates, at a prescribed calibration period Tc of from 10 to 15 minutes, the blood-pressure determining means 88 determines, in advance, a relationship between blood pressure and magnitude of pressure pulse wave, based on the blood-pressure values BP determined by the blood-pressure determining means 88 and magnitudes of the pressure pulse wave PW detected by the active element of the pressure-pulse-wave sensor 46 at any time in a prescribed time duration consisting of a blood-pressure-measurement period in which the blood-pressure values BP are determined by the blood-pressure determining means 88 and respective prescribed time periods preceding and following the blood-pressure-measurement period. FIG. 6 shows an example of the relationship between blood pressure and magnitude of pressure pulse wave. In FIG. 6, symbols $PW_{min}$, $PW_{max}$ indicate a minimal magnitude (i.e., a magnitude of a rising point) and a maximal magnitude (i.e., a magnitude of a peak point) of a heartbeat-synchronous pulse of the pressure pulse wave PW, respectively. The time periods preceding and following the blood-pressure-measurement period are so prescribed that in each of those time periods the blood pressure of the patient does not change so largely from that in the blood-pressure-measurement period, and may include respective time periods immediately before and after the blood-pressure-measurement period.

A blood-pressure monitoring means 92 successively determines, according to the relationship between blood pressure and magnitude of pressure pulse wave, determined by the first relationship determining means 90, a monitor blood pressure MBP of the patient based on a magnitude of each of respective heartbeat-synchronous pulses of the pressure pulse wave PW detected by the active element of the pressure-pulse-wave sensor 46. More specifically described, the monitoring means 92 successively determines, according to the relationship between blood pressure and pressure-pulse-wave magnitude, a monitor diastolic blood pressure $MBP_{DIA}$ of the patient based on a minimal magnitude of each of the pulses of the pressure pulse wave PW, and successively determines, according to the relationship, a monitor systolic blood pressure $MBP_{SYS}$ of the patient based on a maximal magnitude of each of the pulses of the pressure pulse wave PW. In addition, the monitoring means 92 operates the display device 34 to display the thus determined monitor diastolic and systolic blood-pressure values $MBP_{DIA}$, $MBP_{SYS}$.

A pulse-wave-propagation-velocity-related information obtaining means 94 includes a standard-pulse-wave-propagation-velocity-related-information obtaining means 96 and a judgment-pulse-wave-propagation-velocity-related-information obtaining means 98. The standard-pulse-wave-propagation-velocity-related-information obtaining means 96 obtains, as a piece of standard pulse-wave-propagation-velocity-related information, a piece of pulse-wave-propagation-velocity-related information, at any time in the above-described, prescribed time duration consisting of the blood-pressure-measurement period of the blood-pressure determining means 88 and the respective time periods preceding and following the blood-pressure-measurement period, so that a second relationship determining means 100, described below, may determines a relationship between blood pressure and pulse-wave-propagation-velocity-related-information, based on the blood-pressure value BP measured using the cuff 10 and the thus obtained piece of standard pulse-wave-propagation-velocity-related information. The piece of pulse-wave-propagation-velocity-related information may be a time (i.e., a pulse-wave propagation time DT) needed for a pulse wave to propagate from the first portion around which the cuff 10 is wound, to the second portion on which the pressure-pulse-wave sensor 46 is worn, or a velocity (i.e., a pulse-wave propagation velocity PWV) at which the pulse wave to propagate from the first portion to the second portion. For example, the standard-pulse-wave-propagation-velocity-related-information obtaining means 96 determines, as illustrated in FIG. 5, a time difference, i.e., a pulse-wave propagation time DT, between a prescribed periodic point (i.e., a rising point) on a heartbeat-synchronous pulse of the cuff pulse wave KW, and a prescribed periodic point (e.g., a rising point) on a corresponding heartbeat-synchronous pulse of the pressure pulse wave PW. In addition, the information obtaining means 96 determines, based on the thus determined time difference value DT, a pulse-wave propagation velocity PWV, according to the following expression (1) pre-stored in the ROM 31:

$$PWV = L/DT \quad (1)$$

where L is a prescribed constant value representing a difference between a distance from aortic valve to the position where the pressure-pulse-wave sensor 46 is worn, and a distance from the aortic valve to the position where the cuff 10 is worn.

Thus, the standard-pulse-wave-propagation-velocity-related-information obtaining means 96 determines, as a standard pulse-wave propagation time $DT_{ST}$ and a standard pulse-wave propagation velocity $PWV_{ST}$, a pulse-wave propagation time DT and a pulse-wave propagation velocity PWV, respectively, based on the pressure pulse wave PW detected by the pressure-pulse-wave sensor 46, and the cuff pulse wave KW detected by the pulse-wave filter circuit 24, each at a time in the prescribed time duration consisting of the blood-pressure-measurement period and the respective time periods preceding and following the blood-pressure-measurement period.

The judgment-pulse-wave-propagation-velocity-related-information obtaining means 98 operates, at a prescribed judgment period Ta (e.g., 2.5 to 5 minutes) shorter than the calibration period Tc, the cuff-pressure changing means 86 to increase the cuff pressure Pc to the pulse-wave-detection pressure $P_{CM2}$, reads, in this state, the pressure pulse wave PW detected by the pressure-pulse-wave sensor 46 and the cuff pulse wave KW detected by the pulse-wave filter circuit 24, and obtains, like the standard-pulse-wave-propagation-velocity-related-information obtaining means 96, a piece of judgment pulse-wave-propagation-velocity-related information, such as a judgment pulse-wave propagation time $DT_2$ or a judgment pulse-wave propagation velocity $PWV_2$. The judgment period Ta is measured from the end of each blood-pressure-measuring operation in which the blood-pressure determining means 88 determines the blood-pressure values BP of the patient.

The second relationship determining means 100 determines each of two constants $\alpha 1$, $\beta 1$ of the following expression (2) representing a relationship between blood pressure and pulse-wave propagation time, or each of two constants $\alpha 2$, $\beta 2$ of the following expression (3) representing a relationship between blood pressure and pulse-wave propagation velocity, based on a plurality of blood-pressure values BP (e.g., systolic blood-pressure values $BP_{SYS}$, mean blood-pressure values $BP_{MEAN}$, or diastolic blood-pressure values $BP_{DIA}$) determined by the blood-pressure determining means 88 and a plurality of pieces of standard pulse-wave-propagation-velocity-related information obtained by the standard-pulse-wave-propagation-velocity-related-information obtaining means 96:

$$EBP=\alpha 1(DT)+\beta 1 \quad (2)$$

where $\alpha 1$ is a negative constant and $\beta 1$ is a positive constant.

$$EBP=\alpha 2(PWV)+\beta 2 \quad (3)$$

where $\alpha 2$ is a positive constant and $\beta 2$ is a positive constant.

For example, based on a first combination of the systolic blood-pressure value $BP_{SYS}$ determined by the blood-pressure determining means 88 in a current blood-pressure measuring operation and the pulse-wave propagation time DT obtained during the current blood-pressure measuring operation, and a second combination of the systolic blood-pressure value $BP_{SYS}$ determined by the blood-pressure determining means 88 in its preceding blood-pressure measuring operation and the pulse-wave propagation time DT obtained during the preceding blood-pressure measuring operation, the second relationship determining means 100 determines the two constants $\alpha 1$, $\beta 1$ of the expression (2).

An estimated-blood-pressure determining means 102 determines, based on a piece of judgment pulse-wave-propagation-velocity-related information (e.g., a judgment pulse-wave propagation time value DT, or a judgment pulse-wave propagation velocity value PWV), obtained by the judgment-pulse-wave-propagation-velocity-related-information obtaining means 98, an estimated blood-pressure value EBP of the patient, according to the relationship between blood pressure and pulse-wave-propagation-velocity-related information, i.e., the relationship represented by the expression (2) or the expression (3). In the case where the second relationship determining means 100 determines the constants of the expression (2) or the expression (3), based on the systolic blood-pressure values $BP_{SYS}$, the estimated-blood-pressure determining means 102 determines an estimated systolic blood-pressure value $EBP_{SYS}$ of the patient; in the case where the means 100 determines the constants of the expression (2) or the expression (3), based on the mean blood-pressure values $BP_{MEAN}$, the means 102 determines an estimated mean blood-pressure value $EBP_{MEAN}$ of the patient; and in the case where the means 100 determines the constants of the expression (2) or the expression (3), based on the diastolic blood-pressure values $BP_{DIA}$, the means 102 determines an estimated diastolic blood-pressure value $EBP_{MEAN}$ of the patient.

A propagation-velocity-related-information-change-value determining means 104 determines, each time the judgment period Ta periodically elapses after the last blood-pressure measuring operation, a change value of the pieces of pulse-wave-propagation-velocity-related information obtained by the pulse-wave-propagation-velocity-related-information obtaining means 94. Here, the propagation-velocity-related-information change value is defined as a change rate or a change amount of a current piece of judgment pulse-wave-propagation-velocity-related information, obtained at a current time when the judgment period Ta has elapsed, from its preceding piece of judgment pulse-wave-propagation-velocity-related information, obtained at its preceding time when the judgment period Ta had elapsed, or from the piece of standard pulse-wave-propagation-velocity-related information, obtained during the last blood-pressure measuring operation. Since the standard pulse-wave-propagation-velocity-related information is related to the blood pressure BP by the second relationship determining means 100 and the judgment pulse-wave-propagation-velocity-related information is converted into the estimated blood pressure EBP by the estimated-blood-pressure determining means 102, the propagation-velocity-related-information change values may be obtained as change values determined based on the blood-pressure value BP and the estimated blood-pressure values EBP.

A monitor-blood-pressure-change-value determining means 106 determines, each time the judgment period Ta periodically elapses, a change value of the monitor blood-pressure values determined by the blood-pressure monitoring means 92 at respective times when the pieces of pulse-wave-propagation-velocity-related information used to determine the propagation-velocity-related-information change values are obtained.

A relationship checking means 108 compares the propagation-velocity-related-information change value determined by the propagation-velocity-related-information-change-value determining means 94, and the monitor-blood-pressure change value determined by the monitor-blood-pressure-change-value determining means 106, with each other, and judges whether the relationship between blood pressure and pressure pulse wave, determined by the first relationship determining means 100, is appropriate. If the relationship is not appropriate because the pressure pulse wave sensor 46 is inappropriately pressed against the radial artery 56, the monitor blood-pressure values MBP determined by the blood-pressure monitoring means 92 may largely differ from the actual blood pressure of the patient. On the other hand, though the pulse-wave-propagation-velocity-related information is less accurate than the monitor blood-pressure values MBP, the information changes in relation with the change of blood pressure of the patient, and is obtained based on the time difference between the respective periodic points of the cuff pulse wave KW and the pressure pulse wave PW. Thus, the pulse-wave-propagation-velocity-related information is not influenced by the actual state in which the pressure pulse wave sensor 46 is pressed against the radial artery 56. Therefore, it is possible to judge whether the relationship between blood pressure and pressure pulse wave is appropriate, by comparing the propagation-velocity-related-information change value and the monitor-blood-pressure change value with each other. For example, if a relative value of the monitor-blood-pressure change value relative to the propagation-velocity-related-information change value does not fall within a predetermined normal range, the relationship checking means 108 judges that the relationship between blood pressure and pressure pulse wave is not appropriate. The relative value of the monitor-blood-pressure change value may be a difference of the monitor-blood-pressure change value from the propagation-velocity-related-information change value, or a ratio of the monitor-blood-pressure change value to the propagation-velocity-related-information change value. In the case where the relative value of the monitor-blood-pressure change value relative to the propagation-velocity-related-information change value is obtained as the ratio of the monitor-blood-pressure change value to the propagation-velocity-related-information change value, the normal range may range from 0.8 to 1.2.

A normal-range determining means 110 determines, as the normal range, a narrower range, if the estimated diastolic blood-pressure value $MBP_{DIA}$ determined by the blood-pressure monitoring-means 92 when the relationship checking means 108 checks the relationship between blood pressure and pressure pulse wave is smaller than a prescribed danger value (e.g., 70 mmHg) which indicates that the patient needs an urgent treatment. For example, in the case where the normal range ranges from 0.8 to 1.2 as described above, the normal-range determining means 110 narrows the normal range into the narrower range of 0.85 to 1.15.

Figure 7:
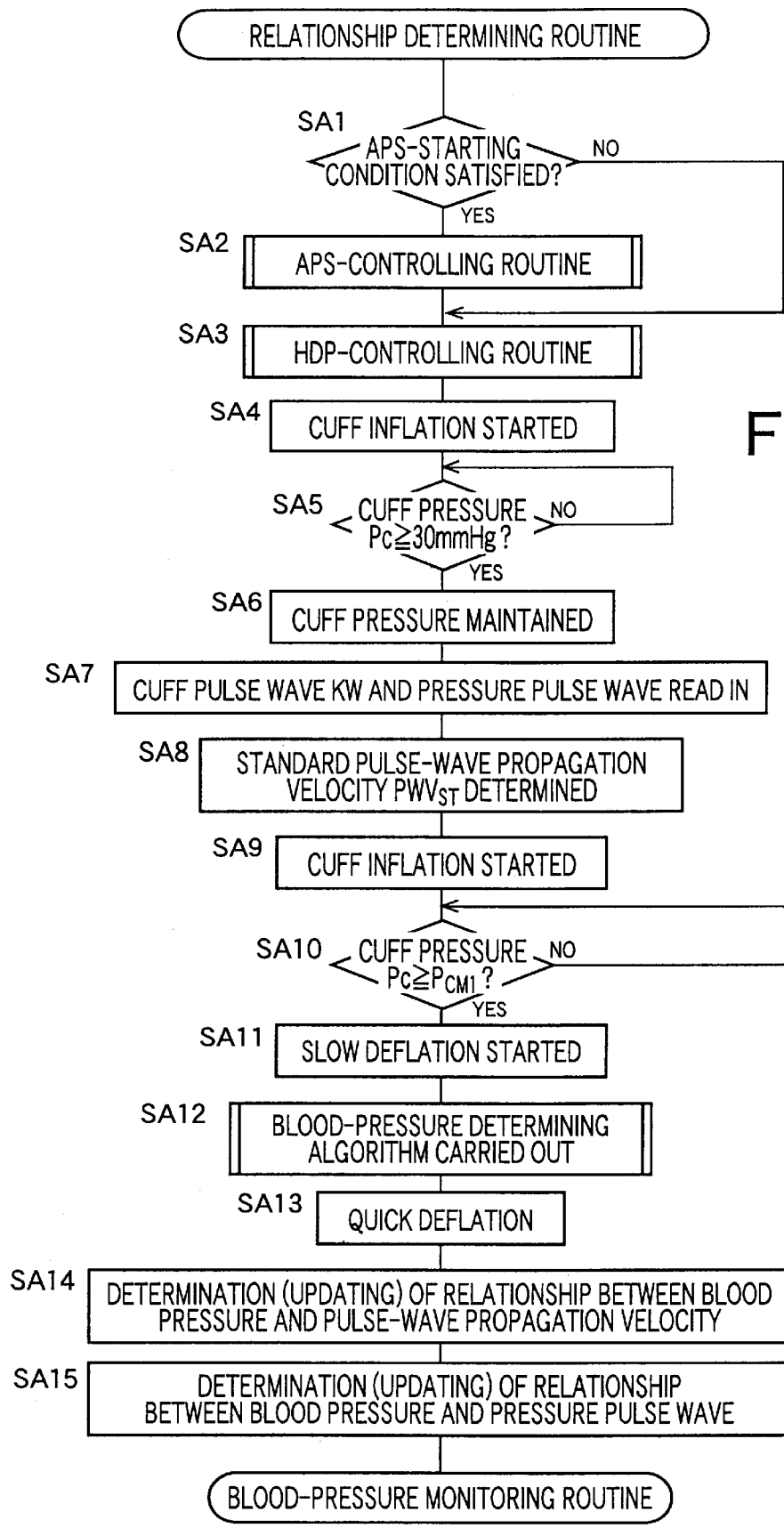
FIG. 7 is a flow chart representing a relationship determining routine according to which the control device shown in FIG. 1 determines a relationship between blood pressure and pressure pulse wave, and a relationship between blood pressure and pulse-wave propagation velocity.
Figure 8:
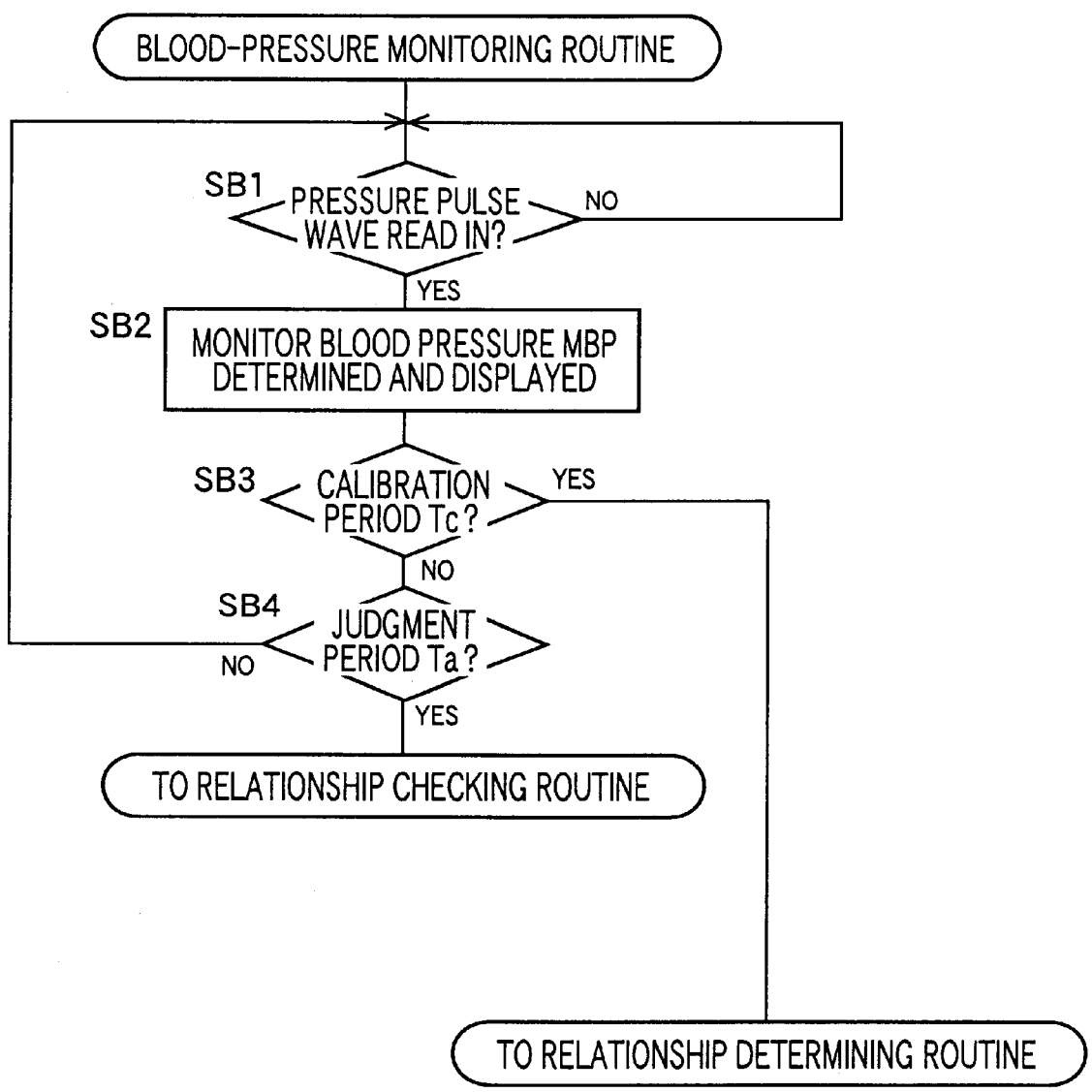
FIG. 8 is a flow chart representing a blood-pressure monitoring routine according to which the control device shown in FIG. 1 successively determines a monitor blood-pressure value MBP.
Figure 9:
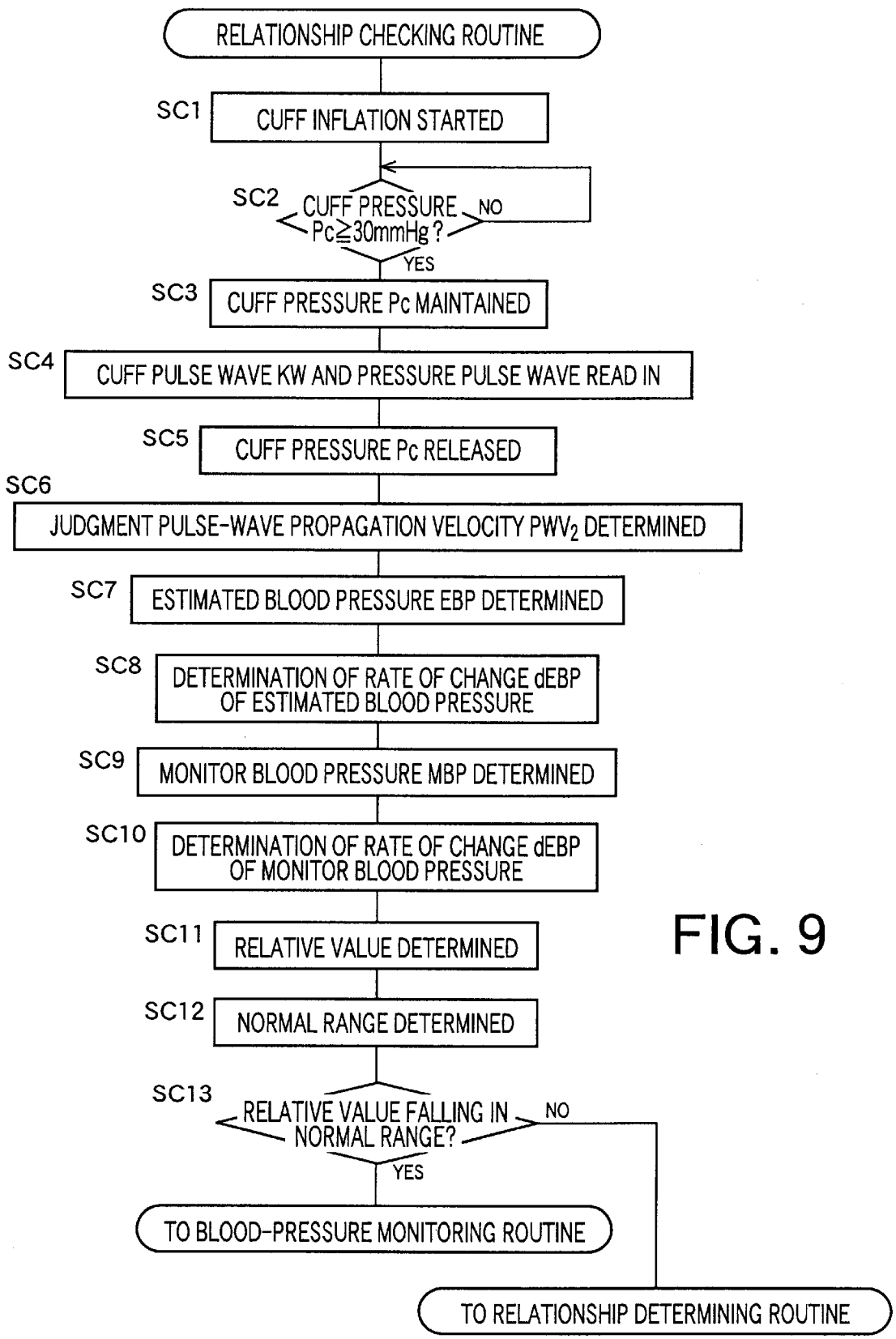
FIG. 9 is a flow chart representing a relationship judging routine according to which the control device shown in FIG. 1 judges whether the relationship between blood pressure and pressure pulse wave is appropriate.

FIGS. 7, 8, and 9 are flow charts representing essential functions of the control device 28 shown in FIG. 3. FIG. 7 shows a relationship determining routine for determining a relationship between blood pressure and pressure pulse wave, and a relationship between blood pressure and pulse-wave propagation velocity; FIG. 8 shows a blood-pressure monitoring routine for continuously determining monitor blood-pressure values MBP of a patient; and FIG. 9 shows a relationship checking routine for judging whether the relationship between blood pressure and pressure pulse wave is appropriate.

According to the relationship determining routine of FIG. 7, first, the control device 28 carries out Step SA1 (hereinafter, "Step" is omitted, if appropriate) where the control device 28 judges whether the prescribed pressing-position changing condition (i.e., the APS-starting condition) has been satisfied, for example, whether one of the pressure-sensing elements, arranged on the press surface 54 of the pressure-pulse-wave sensor 46, that detects the greatest one of the respective amplitudes of the respective pressure pulse waves detected by all the elements is located in either one of the opposite end portions of the array of elements.

If the pressing position where the pressure-pulse-wave sensor 46 is pressed against the radial artery 56 is not appropriate, for example, when the pressure-pulse-wave detecting probe 36 is initially worn on the patient, and accordingly if the prescribed pressing-position changing condition is satisfied, a positive judgment is made at SA1, so that the control proceeds with SA2, i.e., an APS-controlling routine. According to this APS-controlling routine, the control device 28 determines an optimum pressing position where one of the pressure-sensing elements that is located at substantially the middle of the array of elements detects the greatest one of the respective amplitudes of the respective pressure pulse waves detected by all the elements, that is, where one of the pressure-sensing elements that detects the greatest one of the respective amplitudes of the respective pressure pulse waves detected by all the elements, is located at substantially the middle of the array of elements. In addition, the control device 28 determines, as an active element, the one pressure-sensing element located at substantially the middle of the array of elements. Since at SA1 and SA2, the pressing position where the pressure-pulse-wave sensor 46 is pressed is determined, SA1 and SA2 correspond to the optimum-pressing-position determining means 80.

On the other hand, if a negative judgment is made at SA1 because the pressure-pulse-wave sensor 46 is appropriately positioned relative to the radial artery 56, or after SA2, the control goes to SA3, i.e., an HDP-controlling routine corresponding to the optimum-pressing-force determining means 82 and the optimum-pressing-force maintaining means 84.

More specifically described, the control device 28 continuously increases the pressing force $P_{HDP}$ applied to the pressure-pulse-wave sensor 46, and determines, as an optimum pressing force $P_{HDPO}$, a value of the pressing force $P_{HDP}$ at the time when the active element of the sensor 46, positioned right above the radial artery 56, detects the greatest one of respective amplitudes of respective heartbeat-synchronous pulses of the pressure pulse wave PW(t), and replaces the prior optimum pressing force with the thus determined new optimum pressing force $P_{HDPO}$. Then, the pressing force $P_{HDP}$ applied to the sensor 46 is maintained at the new optimum pressing force $P_{HDPO}$. In the state in which the pressure-pulse-wave sensor 46 is pressed with the new optimum pressing force $P_{HDPO}$, the control device 28 carries out SA4 and the following steps.

Subsequently, the control goes to SA4, SA5, and SA6 corresponding to the cuff-pressure changing means 86. First, at SA4, the control device 28 switches the deflation control valve 16 to its pressure-supply position, and operates the air pump 18, so that the pressure in the cuff 10 is quickly increased.

At SA5, the control device 28 judges whether the cuff pressure Pc has reached the pulse-wave-detection pressure $P_{CM2}$, i.e., 30 mmHg. If a negative judgment is made at SA5, SA5 is repeated. If a positive judgment is made at SA5, then the control goes to SA6 to stop the air pump 18 and switch the deflation control valve 16 to its pressure-maintain position, so that the cuff pressure Pc is maintained at about 30 mmHg.

Then, at SA7, the control device 28 reads in respective lengths of the cuff pulse wave KW detected by the pulse-wave filter circuit 24 and the pressure pulse wave PW detected by the pressure-pulse-wave sensor 46, each of those lengths corresponding to one heartbeat of the patient.

Subsequently, the control goes to SA8 corresponding to the standard-pulse-wave-propagation-velocity-relatedinformation obtaining means 96. At SA8, the control device 28 determines respective rising points of the respective heartbeat-synchronous pulses of the cuff pulse wave KW and the pressure pulse wave PW read in at SA7, and determines, as a standard pulse-wave propagation time $DT_{ST}$, a time difference between the thus determined rising points. I addition, the control device 28 determines a standard pulse-wave propagation velocity $PWV_{ST}$, based on the thus determined standard pulse-wave propagation time $DT_{ST}$, according to the previously-explained expression (1).

Then, the control goes to SA9, SA10, and SA11 corresponding to the cuff-pressure changing means 86. At SA9, the control device 28 switches the deflation control valve 16 to its pressure-supply position, and operates the air pump 18, so that the pressure in the cuff 10 is quickly increased for a blood-pressure measuring operation. At SA10, the control device 28 judges whether the cuff pressure Pc has reached the prescribed target pressure $P_{CM1}$, i.e., 180 mmHg. If a negative judgment is made at SA10, SA10 is repeated. If a positive judgment is made at SA10, then the control goes to SA11 to stop the air pump 18 and switch the deflation control valve 16 to its slow-deflation position, so that the pressure in the cuff 10 is slowly decreased at a prescribed rate of 3 mmHg/sec.

Then, at SA12 corresponding to the blood-pressure determining means 88, the control device 28 determines a systolic blood-pressure value $BP_{SYS}$, a mean blood-pressure value $BP_{MEAN}$, and a diastolic blood-pressure value $BP_{DIA}$ of the patient, based on the change of respective amplitudes of respective heartbeat-synchronous pulses of the cuff pulse wave KW represented by the cuff-pulse-wave signal $SM_1$ continuously obtained during the slow decreasing of the cuff pressure Pc, according to well-known oscillometric-type blood-pressure determining algorithm. The thus determines blood-pressure values BP are displayed on the display device 34. Then, at SA13, the control device 28 switches the deflation control valve 16 to its quick-deflation position, so that the pressure in the cuff 10 is quickly released.

Then, the control goes to SA14 corresponding to the second relationship determining means 100. At SA14, the control device 28 determines or updates the constant values $\alpha 2$, $\beta 2$ of the expression (3), based on a first combination of the standard pulse-wave propagation velocity $PWV_{ST}$ determined at SA8, and the diastolic blood-pressure value $BP_{DIA}$ determined at SA12, in in the current control cycle according to this relationship determining routine, and a second combination of the standard pulse-wave propagation velocity $PWV_{ST}$ determined at SA8, and the diastolic blood-pressure value $BP_{DIA}$ determined at SA12, in in the preceding control cycle according to this routine. In the case where the current control cycle is an initial control cycle according to this routine, the control device 28 employs, as the above-indicated second combination, a standard combination of a standard pulse-wave propagation velocity $PWV_{ST}$ and a diastolic blood-pressure value $BP_{DIA}$ that is pre-stored in the ROM 31.

Subsequently, the control goes to SA15 corresponding to the first relationship determining means 90. At SA15, the control device 28 determines or updates the relationship between blood pressure and pressure pulse wave, shown in FIG. 6, based on a minimal value $PW_{min}$ and a maximal value $PW_{max}$ of the one heartbeat-synchronous pulse of the pressure pulse wave PW read in at SA7, and the diastolic and systolic blood-pressure values $BP_{DIA}$, $BP_{SYS}$ determined at SA12. SA15 is followed by the blood-pressure monitoring routine of FIG. 8.

Next, the blood-pressure monitoring routine of FIG. 8 will be described. At SB1 of FIG. 8, the control device 28 judges whether the control device has read in one heartbeat-synchronous pulse of the pressure pulse wave PW(t). If a negative judgment is made at SB1, SB1 is repeated. Meanwhile, if a positive judgment is made at SB1, the control goes to SB2 corresponding to the blood-pressure monitoring means 92.

At SB2, the control device 28 determines, according to the relationship between blood pressure and pressure pulse wave, determined at SA15 of FIG. 7, a monitor diastolic blood-pressure value $MBP_{DIA}$ and a monitor systolic blood-pressure value $MBP_{SYS}$ of the patient, based on a minimal value $PW_{min}$ and a maximal value $PW_{max}$ of the one heartbeat-synchronous pulse of the pressure pulse wave PW read in at SB1, and operates the display device 34 to display the thus determined monitor diastolic and systolic blood-pressure values $MBP_{DIA}$, $MBP_{SYS}$.

Then, at SB3, the control device 28 judges whether the prescribed calibration period Tc, e.g., from 10 to 30 minutes has elapsed after the determination of the blood-pressure values BP at SA12 of FIG. 7. If a positive judgment is made at SB3, the control goes to the relationship determining routine of FIG. 7.

On the other hand, if a negative judgment is made at SB3, the control goes to SB4 to judge whether the judgment period Ta, i.e., 2.5 minutes has elapsed after the determination of the blood-pressure values BP at SA12 of FIG. 7, or after the relationship checking routine of FIG. 9, described later, has carried out. If a negative judgment is made at SB4, the control goes back to SB1 and the following steps. On the other hand, if a positive judgment is made at SB4, the control device 28 carries out the relationship checking routine of FIG. 9.

Next, the relationship checking routine of FIG. 9 will be described. SC1, SC2, and SC3 of FIG. 9 corresponding to the cuff-pressure changing means 86 are the same as SA4, SA5, and SA6 of FIG. 7. Thus, the cuff pressure Pc is maintained at 30 mmHg.

Then, at SC4, the control device 28 reads in respective lengths of the cuff pulse wave KW detected by the pulse-wave filter circuit 24 and the pressure pulse wave PW detected by the pressure-pulse-wave sensor 46, each of those lengths corresponding to one heartbeat of the patient. Then, at SC5 corresponding to the cuff-pressure changing means 86, the control device 28 switches the deflation control valve 16 to its quick-deflation position.

Next, at SC6 corresponding to the judgment-pulse-wave-propagation-velocity-related-information obtaining means 98, the control device 28 determines, like done at SA8 of FIG. 7, a judgment pulse-wave propagation velocity $PWV_2$, based on respective rising points of the respective heartbeat-synchronous pulses of the cuff pulse wave KW and the pressure pulse wave PW read in at SC5.

Then, at SC7 corresponding to the estimated-blood-pressure determining means 102, the control device 28 determines, according to the expression (3) determined or updated at SA14 of FIG. 7, an estimated diastolic blood pressure $EBP_{DIA}$ of the patient based on the judgment pulse-wave propagation velocity $PWV_2$ determined at SC6.

Subsequently, at SC8, the control device 28 determines a rate of change $dEBP_{DIA}$ of the estimated diastolic blood-pressure value $EBP_{DIA}$ determined at SC7 from the diastolic blood-pressure value $BP_{DIA}$ determined at SA12 of FIG. 7. Since the estimated-diastolic-blood-pressure change rate $dEBP_{DIA}$ is a sort of propagation-velocity-related-information change value, SC8 corresponds to the propagation-velocity-related-information-change-value determining means 104.

Then, the control goes to SC9 corresponding to the blood-pressure monitoring means 92, the control device 28 determines, according to the relationship between blood pressure and pressure pulse wave, determined or updated at SA15 of FIG. 7, a monitor diastolic blood-pressure value $MBP_{DIA}$ of the patient based on a minimal magnitude $PW_{min}$ of the one heartbeat-synchronous pulse of the pressure pulse wave PW read in at SC4.

Next, at SC10 corresponding to the monitor-blood-pressure-change-value determining means 106, the control device 28 determines a rate of change $dMBP_{DIA}$ of the monitor diastolic blood-pressure value $MBP_{DIA}$ determined at SC9 from the diastolic blood-pressure value $BP_{DIA}$ determined at SA12 of FIG. 7.

At SC11, the control device 28 determines a ratio of the rate of change $dMBP_{DIA}$ of the monitor diastolic blood-pressure value $MBP_{DIA}$, determined at SC10, to the rate of change $dEBP_{DIA}$ of the estimated diastolic blood-pressure value $EBP_{DIA}$, determined at SC8, as the relative value of the monitor-blood-pressure change value relative to the estimated-blood-pressure change value.

Then, at SC12 corresponding to the normal-range determining means 110, the control device 28 judges whether the monitor blood-pressure value $MBP_{DIA}$ determined at SC9 is smaller than a prescribed danger value, i.e., 70 mmHg and, if a positive judgment is made, narrows the standard normal range of from 0.8 to 1.2 to be used at SC13 to check the relationship between blood pressure and pressure pulse wave, into the narrower normal range of from 0.85 to 1.15.

Then, the control goes to SC13 corresponding to the relationship checking means 108. At SC13, the control device 28 judges whether the relative value (i.e., the ratio) determined at SC11 falls within the standard or narrower normal range determined at SC12. A positive judgment made at SC12 indicates that the relationship between blood pressure and pressure pulse wave is appropriate and accordingly the monitor blood-pressure values MBP are accurate. Therefore, the control goes to the blood-pressure monitoring routine of FIG. 8. On the other hand, a negative judgment made at SC12 indicates that the relationship between blood pressure and pressure pulse wave is not appropriate and accordingly the monitor blood-pressure values MBP are not accurate. Therefore, the control goes to the relationship determining routine of FIG. 7, so that the pressure-pulse-wave sensor 46 is appropriately pressed against the radial artery 56 and the relationship between blood pressure and pressure pulse wave is updated.

In the illustrated embodiment in which the above-described flow charts are employed, at SC6 (the pulse-wave-propagation-velocity-related-information obtaining means 94), the control device 28 determines the judgment pulse-wave propagation velocity $PWV_2$, between the cuff 10 and the pressure-pulse-wave sensor 46; and at SC8 (the propagation-velocity-related-information-change-value determining means 104), the control device 28 determines, at the judgment period Ta, the rate of change dEBP of the estimated blood-pressure value as the relative value of the judgment pulse-wave propagation velocity $PWV_2$. Since the judgment pulse-wave propagation velocity $PWV_2$ changes with the change of blood pressure of the patient, the rate of change dEBP of the estimated blood-pressure value also changes with the change of blood pressure. In addition, the rate of change dMBP of the monitor blood-pressure value determined at SC10 (the monitor-blood-pressure-change-value determining means 106), also changes with the change of blood pressure. However, in the case where the condition under which the pressure-pulse-wave 46 is worn on the patient has changed and the monitor blood-pressure value MBP determined at SB2 (the blood-pressure monitoring means 92) are not accurate, the rate of change dMBP of the monitor blood-pressure value largely differs from the rate of change dEBP of the estimated blood-pressure value. Therefore, at SC13 (the relationship checking means 108), the control device 28 compares the rate of change dMBP of the monitor blood-pressure value and the rate of change dEBP of the estimated blood-pressure value, with each other, and judges whether the relationship between blood pressure and pressure pulse wave, determined at SC15 (the first relationship determining means 90) is appropriate.

Therefore, a longer calibration period Tc can be employed to carry out SA12 (the blood-pressure determining means 88) and thereby update the relationship between blood pressure and pressure pulse wave, and accordingly the discomfort the patient feels can be reduced. In addition, since the pulse-wave propagation velocity PWV is determined based on the cuff pulse wave WK detected in the state in which the pressure of the cuff 10 is 30 mmHg, the patient feels little discomfort when the pulse-wave propagation velocity PWV is determined. Moreover, since the pulse-wave propagation velocity PWV can be determined even if the pressure-pulse-wave sensor 46 is not worn on the downstream side of the cuff 10, the sensor 46 can be worn on the other arm than the arm around which the cuff 10 is wound.

In addition, in the embodiment in which the above-described flow charts are employed, at SC12 (the normal-range determining means 110), the control device 28 determines, when the monitor blood-pressure value MBP is lower than 70 mmHg, the narrower normal range than the standard normal range determined when the monitor blood-pressure value MBP is not lower than 70 mmHg, so that the narrower normal range is used at SC13 (the relationship checking means 108). Thus, when the monitor blood-pressure value MBP is lower than 70 mmHg, whether the relationship between blood pressure and pressure pulse wave is appropriate or not is more strictly checked. Therefore, the accuracy of the monitor blood-pressure values MBP determined when the blood pressure of the patient is low can be improved, and whether the blood pressure of the patient is so low as to need an urgent treatment can be judged quickly and reliably.

Moreover, in the embodiment in which the above-described flow charts are employed, when the relationship between blood pressure and pressure pulse wave is judged as not appropriate at SC13 (the relationship checking means 108), the control device 28 replaces the inappropriate relationship with a new, appropriate relationship, at SA15 (the first relationship determining means 90). Thus, accurate monitor blood-pressure values MBP can be successively determined according to the thus updated relationship, and the reliability of continuous monitoring of blood pressure of the patient can be improved.

Next, there will be described another or second embodiment of the present invention. The same reference numerals as used in the first embodiment shown in FIGS. 1 to 9 are used to designate the corresponding elements of the second embodiment, and the description thereof is omitted.

Figure 10:
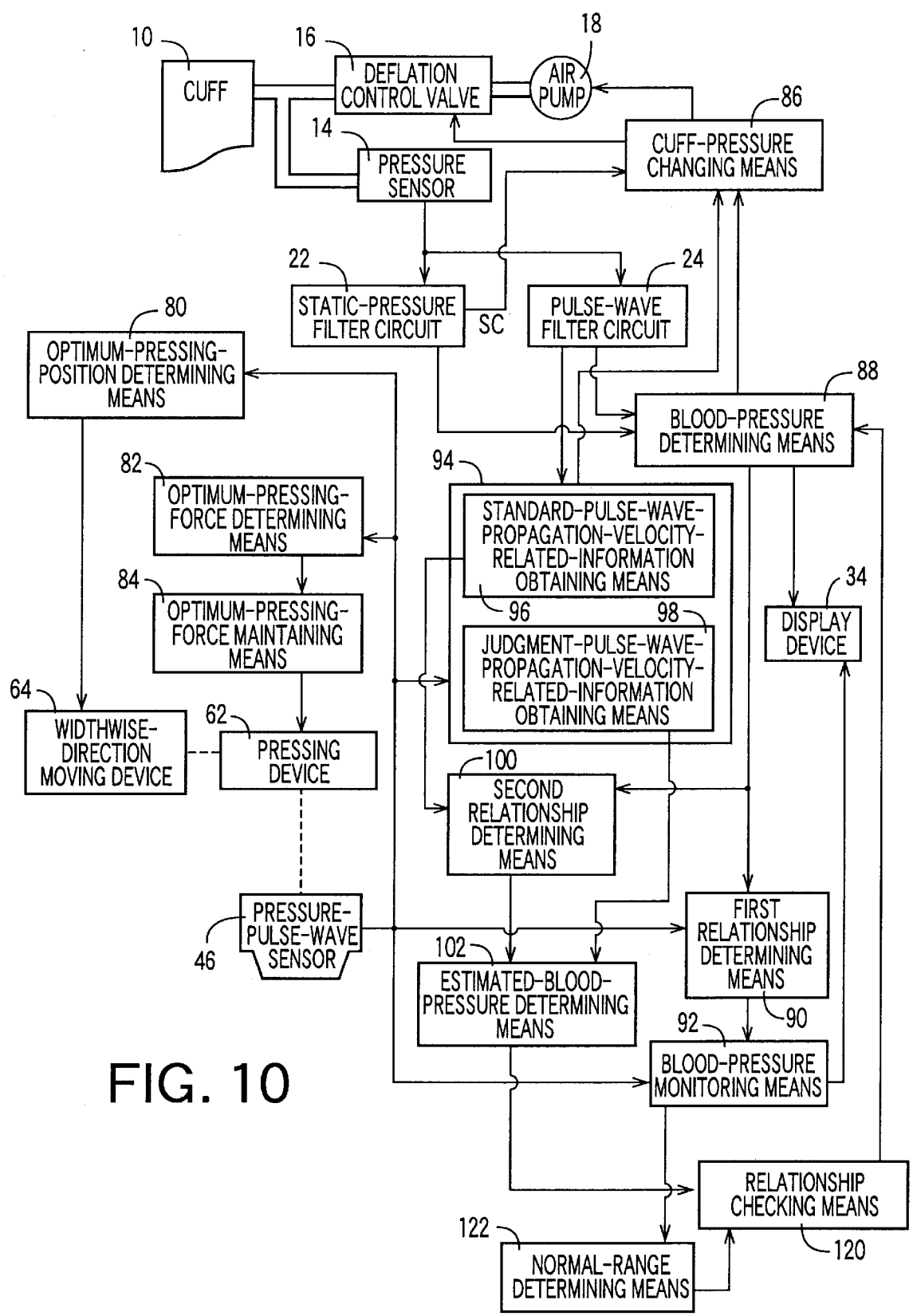
FIG. 10 is a block diagram corresponding to FIG. 2, for explaining essential functions of another control device of another continuous blood-pressure monitoring apparatus as a second embodiment of the present invention.

The second embodiment relates to a continuous blood-pressure monitoring apparatus which differs from the continuous blood-pressure monitoring apparatus 8 shown in FIG. 1 only with respect to control functions of a control device 28. FIG. 10 shows a block diagram for explaining essential control functions of the control device 28 employed in the second embodiment.

The block diagram shown in FIG. 10 differs from the block diagram shown in FIG. 3, only in that the block diagram of FIG. 10 does not employ the propagation-velocity-related-information-change-value determining means 104 or the monitor-blood-pressure-change-value determining means 106, and employs a relationship checking means 120 and a normal-range determining means 122 in place of the relationship checking means 108 and the normal-range determining means 110 employed in the block diagram of FIG. 3. The relationship checking means 120 and the normal-range determining means 122 will be described below.

The relationship checking means 120 directly compares an estimated blood-pressure value EBP determined by the estimated-blood-pressure determining means 102, and a monitor blood-pressure value MBP determined by the blood-pressure monitoring means 92 based on a magnitude of a heartbeat-synchronous pulse of the pressure pulse wave PW detected by the pressure-pulse-wave sensor 46 in a time duration in which the pressure of the cuff 10 is maintained at the pulse-wave-detection pressure $P_{CM2}$ or in a prescribed time duration preceding or following that time duration (i.e., detected at a time around the time of detection of a heartbeat-synchronous pulse of the pressure pulse wave PW used to determine the estimated blood-pressure value EBP), with each other, and judges whether a relationship between blood pressure and pressure pulse wave, determined by the first relationship determining means 90 is appropriate. For example, the relationship checking means 120 judges that the relationship between blood pressure and pressure pulse wave is not appropriate, if a relative value of the monitor blood-pressure value MBP relative to the estimated blood-pressure value EBP does not fall within a predetermined normal range. The above-indicated relative value may be a difference of between the monitor blood-pressure value MBP and the estimated blood-pressure value EBP, or a ratio of one of the two values MBP, EBP to the other. In the case where the ratio is employed as the relative value, the normal range may be predetermined such that the normal range ranges from 0.8 to 1.2.

The normal-range determining means 122 determines a narrower normal range narrower than the above-indicated standard normal range, if at least one of the estimated blood-pressure value EBP determined by the estimated-blood-pressure determining means 102 and the monitor blood-pressure value MBP determined by the blood-pressure monitoring means 92 for the checking or judging of the relationship checking means 120 is lower than the previously-explained danger value.

Figure 11:
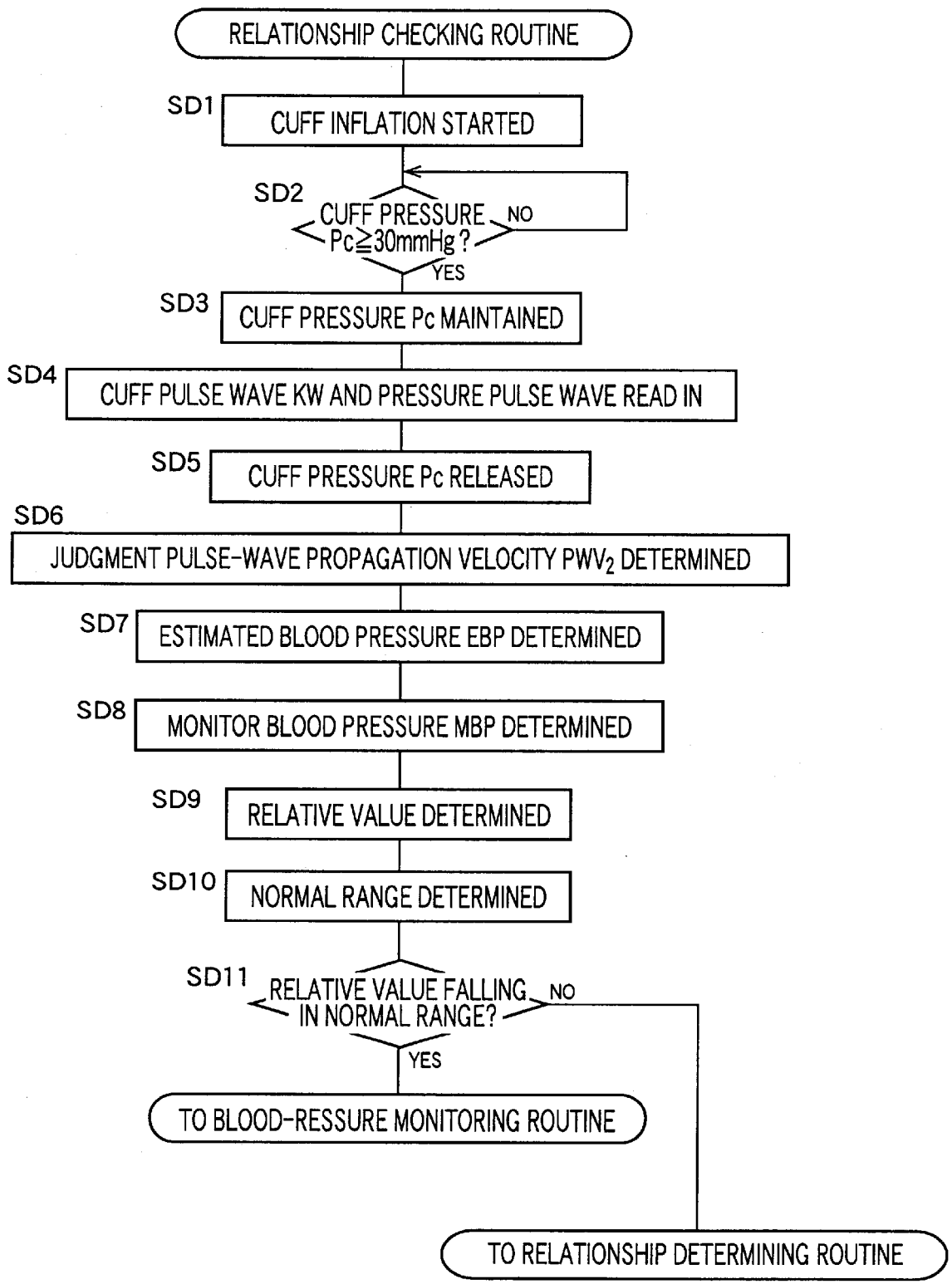
FIG. 11 is a flow chart representing a relationship judging routine according to which the control device shown in FIG. 10 judges whether a relationship between blood pressure and pressure pulse wave is appropriate.

FIG. 11 is a flow chart representing essential functions of the control device 28 shown in FIG. 10. More specifically described, FIG. 11 shows a relationship checking routine for judging whether the relationship between blood pressure and pressure pulse wave is appropriate. In addition, the control device 28 is operated according to the relationship determining routine of FIG. 7 and the blood-pressure monitoring routine of FIG. 8.

In FIG. 11, SD1 to SD7 are identical with SC1 to SC7 of FIG. 9. Thus, the control device 28 determines an estimated diastolic blood-pressure value $EBP_{DIA}$. At SD8 identical with SC9, the control device 28 determines a monitor diastolic blood-pressure value $MBP_{DIA}$.

Then, at SD9, the control device 28 determines a ratio of the monitor diastolic blood-pressure value $MBP_{DIA}$ determined at SD9 to the estimated diastolic blood-pressure value $EBP_{DIA}$ determined at SD7, as a relative value of the value $MBP_{DIA}$ to the value $EBP_{DIA}$.

Next, at SD10 corresponding to the normal-range determining means 122, the control device 28 judges whether at least one of the estimated diastolic blood-pressure value $EBP_{DIA}$ determined at SD7 and the monitor diastolic blood-pressure value $MBP_{DIA}$ determined at SD9 is lower than the prescribed danger value, i.e., 70 mmHg. If a positive judgment is made, the control device 28 determines, as the normal range to be used at SD11 to check the relationship between blood pressure and pressure pulse wave, a narrower normal range than the standard normal range determined if a negative judgment is made. In the case where the standard normal range ranges from 0.8 to 1.2, the narrower range may range from 0.85 to 1.15.

Subsequently, the control goes to SD11 corresponding to the relationship checking means 120. At SD11, the control device 28 judges whether the relative value determined at SD9 falls within the normal range determined at SD10. If a positive judgment is made at SD11, the control goes to the blood-pressure monitoring routine of FIG. 8. On the other hand, a negative judgment made at SD11 indicates that the relationship between blood pressure and pressure pulse wave is not appropriate and accordingly the accuracy of the monitor blood-pressure value MBP is not sufficient. Hence, the control goes to the relationship determining routine of FIG. 7, so that the pressure-pulse-wave sensor 46 is pressed again appropriately and the relationship between blood pressure and pressure pulse wave is updated.

In the illustrated embodiment in which the above-described flow chart is employed, at SD7 (the estimated-blood-pressure determining means 102), the control device 28 determines the estimated blood-pressure value EBP based on the judgment pulse-wave propagation velocity $PWV_2$ according to the relationship between blood pressure and pulse-wave-propagation-velocity-related information. If the condition under which the pressure-pulse-wave sensor 46 is worn on the patient has changed and accordingly the monitor blood-pressure value MBP determined at SD8 (the blood-pressure monitoring means 92) is not accurate, the monitor blood-pressure value MBP largely differs from the estimated blood-pressure value EBP. Hence, at SD11 (the relationship checking means 120), the control device 28 compares the estimated blood-pressure value EBP and the monitor blood-pressure value MBP determined based on the pressure pulse wave PW at SD8 (the blood-pressure monitoring means 92), with each other, and judges whether the relationship between blood pressure and pressure pulse wave, determined at SA15 (the first relationship determining means 90) is appropriate or not.

Therefore, a longer calibration period Tc can be employed to carry out SA12 (the blood-pressure determining means 88) and thereby update the relationship between blood pressure and pressure pulse wave, and accordingly the discomfort the patient feels can be reduced. In addition, since at SD1 to SD3 (the cuff-pressure changing means 86) the judgment pulse-wave propagation velocity $PWV_2$ is determined based on the cuff pulse wave WK detected in the state in which the pressure Pc of the cuff 10 is maintained at the value sufficiently lower than the diastolic blood pressure of the patient, the patient feels minimized discomfort only. Moreover, since the standard pulse-wave propagation velocity $PWV_{ST}$ used to determine the relationship between blood pressure and pulse-wave-propagation-velocity-related information, and the judgment pulse-wave propagation velocity $PWV_2$ used to determine the estimated blood-pressure value EBP can each be determined even if the pressure-pulse-wave sensor 46 is not worn on the downstream side of the cuff 10, the sensor 46 can be worn on the other arm than the arm around which the cuff 10 is wound.

While the present invention has been described in its preferred embodiments by reference to the drawings, it is to be understood that the invention may otherwise be embodied.

For example, in the illustrated embodiment, the pressure-pulse-wave sensor 46 is worn on the wrist 43 of the other arm than the arm around which the cuff 10 is wound. However, the sensor 46 may be worn on the wrist of the arm around which the cuff 10 is wound.

While the present invention has been described in detail in its preferred embodiments by reference to the drawings, it is to be understood that the present invention is not limited to those details of the described embodiments and may be embodied with other changes and improvements that may occur to a person skilled in the art without departing from the spirit and scope of the invention defined in the appended claims.

What is claimed is:

1. An apparatus for continuously monitoring a blood pressure of a living subject, comprising:

an inflatable cuff which is adapted to be wound around a portion of the subject, a cuff pulse wave including a plurality of heartbeat-synchronous pulses occurring to the cuff while a pressure in the cuff is changed;

a blood-pressure determining means for determining a blood pressure of the subject based on a signal obtained while the pressure of the cuff is changed;

a pressure-pulse-wave detecting device which includes a pressure-pulse-wave sensor that is adapted to be pressed against an artery of the subject and which continuously detects, through the pressure-pulse-wave sensor, a pressure pulse wave that is produced by the artery and includes a plurality of heartbeat-synchronous pulses;

a relationship determining means for determining a relationship between blood pressure and magnitude of pressure pulse wave, based on the blood pressure determined by the blood-pressure determining means and a magnitude of the pressure pulse wave detected by the pressure-pulse-wave detecting device;

a blood-pressure monitoring means for iteratively determining, according to the thus determined relationship, a monitor blood-pressure value of the subject based on a magnitude of each of the heartbeat-synchronous pulses of the pressure pulse wave detected by the pressure-pulse-wave detecting device;

a pulse-wave-propagation-velocity-related-information obtaining means for iteratively obtaining, in a state in which the pressure of the cuff is held at a prescribed pulse-wave-detection pressure lower than a diastolic blood pressure of the subject, a piece of pulse-wave-propagation-velocity-related information which is related to a velocity at which a pulse wave propagates through the artery of the subject, based on a time of occurrence of a prescribed periodic point of a heartbeat-synchronous pulse of the cuff pulse wave and a time of occurrence of a prescribed periodic point of a corresponding heartbeat-synchronous pulse of the pressure pulse wave;

a propagation-velocity-related-information-change-value determining means for periodically determining, at a prescribed judgment period, a change value of the pieces of pulse-wave-propagation-velocity-related information obtained by the pulse-wave-propagation-velocity-related-information obtaining means;

a monitor-blood-pressure-change-value determining means for periodically determining, at the judgment period, a change value of the monitor blood-pressure values determined by the blood-pressure monitoring means; and a relationship checking means for comparing the change value of the pieces of pulse-wave-propagation-velocity-related information, determined by the propagation-velocity-related-information-change-value determining means, and the change value of the monitor blood-pressure values, determined by the monitor-blood-pressure-change-value determining means, with each other, and thereby judging whether the relationship between blood pressure and magnitude of pressure pulse wave, determined by the relationship determining means, is appropriate.

2. An apparatus for continuously monitoring a blood pressure of a living subject, comprising:

an inflatable cuff which is adapted to be wound around a portion of the subject, a cuff pulse wave including a plurality of heartbeat-synchronous pulses occurring to the cuff while a pressure in the cuff is changed;

a blood-pressure determining means for determining a blood pressure of the subject based on a signal obtained while the pressure of the cuff is changed;

a pressure-pulse-wave detecting device which includes a pressure-pulse-wave sensor that is adapted to be pressed against an artery of the subject and which continuously detects, through the pressure-pulse-wave sensor, a pressure pulse wave that is produced by the artery and includes a plurality of heartbeat-synchronous pulses;

a first relationship determining means for determining a first relationship between blood pressure and magnitude of pressure pulse wave, based on the blood pressure determined by the blood-pressure determining means and a magnitude of the pressure pulse wave detected by the pressure-pulse-wave detecting device;

a blood-pressure monitoring means for successively determining, according to the thus determined first relationship, a monitor blood-pressure value of the subject based on a magnitude of each of the heartbeat-synchronous pulses of the pressure pulse wave detected by the pressure-pulse-wave detecting device;

a standard-pulse-wave-propagation-velocity-related-information obtaining means for obtaining, as a standard piece of pulse-wave-propagation-velocity-related information, a piece of pulse-wave-propagation-velocity-related information which is related to a velocity at which a pulse wave propagates through the artery of the subject, based on a time of occurrence of a prescribed periodic point of a heartbeat-synchronous pulse of the cuff pulse wave in a first time duration comprising at least one of a first time period in which the pressure of the cuff is changed, a prescribed preceding time period preceding the first time period, and a prescribed following time period following the first time period, and a time of occurrence of a prescribed periodic point of a corresponding heartbeat-synchronous pulse of the pressure pulse wave in the first time duration;

a second relationship determining means for determining a second relationship between blood pressure and pulse-wave-propagation-velocity-related information, based on the blood pressure determined by the blood-pressure determining means and the standard piece of pulse-wave-propagation-velocity-related information obtained by the standard-pulse-wave-propagation-velocity-related-information obtaining means;

a cuff-pressure changing means for periodically increasing, at a prescribed judgment period, the pressure of the cuff up to a prescribed pulse-wave-detection pressure lower than a diastolic blood pressure of the subject;

a judgment-pulse-wave-propagation-velocity-related-information obtaining means for obtaining, as a judgment piece of pulse-wave-propagation-velocity-related information, a piece of pulse-wave-propagation-velocity-related information which is related to the velocity at which the pulse wave propagates through the artery of the subject, based on a time of occurrence of a prescribed periodic point of a heartbeat-synchronous pulse of the cuff pulse wave occurring to the cuff in a state in which the pressure of the cuff is held at the pulse-wave-detection pressure by the cuff-pressure changing means, and a time of occurrence of a prescribed periodic point of a corresponding heartbeat-synchronous pulse of the pressure pulse wave detected by the pressure-pulse-wave detecting device in said state;

an estimated-blood-pressure determining means for determining, according to the second relationship, an estimated blood-pressure value of the subject based on the judgment piece of pulse-wave-propagation-velocity-related information obtained by the judgment-pulse-wave-propagation-velocity-related-information obtaining means; and a relationship checking means for comparing the estimated blood-pressure value determined by the estimated-blood-pressure determining means, and a monitor blood-pressure value determined by the blood-pressure monitoring means based on a magnitude of a heartbeat-synchronous pulse of the pressure pulse wave detected by the pressure-pulse-wave detecting device in a second time duration comprising at least one of a second time period in which the pressure of the cuff is held at the pulse-wave-detection pressure by the cuff-pressure changing means, a prescribed preceding time period preceding the second time period, and a prescribed following time period following the second time period, with each other, and thereby judging whether the relationship between blood pressure and magnitude of pressure pulse wave, determined by the first relationship determining means, is appropriate.

3. An apparatus according to claim 1, wherein the relationship checking means judges that the relationship between blood pressure and magnitude of pressure pulse wave is not appropriate, when a relative value between the change value of the pieces of pulse-wave-propagation-velocity-related information, determined by the propagation-velocity-related-information-change-value determining means, and the change value of the monitor blood-pressure values, determined by the monitor-blood-pressure-change-value determining means, does not fall within a normal range, and wherein the apparatus further comprises a normal-range determining means for determining, as the normal range, a narrower range when the monitor blood-pressure value used to determine the change value of the monitor blood-pressure values is lower than a prescribed danger value which indicates that the subject needs an urgent treatment, than a range determined thereby when the monitor blood-pressure value is not lower than the danger value.

4. An apparatus according to claim 2, wherein the relationship checking means judges that the relationship between blood pressure and magnitude of pressure pulse wave is not appropriate, when a relative value between the estimated blood-pressure value determined by the estimated-blood-pressure determining means, and a monitor blood-pressure value determined by the blood-pressure monitoring means based on a magnitude of a heartbeat-synchronous pulse of the pressure pulse wave detected by the pressure-pulse-wave detecting device in the second time period in which the pressure of the cuff is held at the pulse-wave-detection pressure by the cuff-pressure changing means, does not fall within a normal range, and wherein the apparatus further comprises a normal-range determining means for determining, as the normal range, a narrower range when at least one of the estimated blood-pressure value and the monitor blood-pressure value is lower than a prescribed danger value which indicates that the subject needs an urgent treatment, than a range determined thereby when each of the estimated blood-pressure value and the monitor blood-pressure value is not lower than the danger value.

5. An apparatus according to claim 1, wherein the relationship checking means comprises means for operating, when it is judged that the relationship between blood pressure and magnitude of pressure pulse wave is not appropriate, the relationship determining means to update said relationship.

6. An apparatus according to claim 2, wherein the relationship checking means comprises means for operating, when it is judged that the first relationship between blood pressure and magnitude of pressure pulse wave is not appropriate, the first relationship determining means to update the first relationship.

7. An apparatus according to claim 1, further comprising:

a pressure changing device which changes the pressure of the cuff;

a pressure sensor which detects the pressure of the cuff changed by the pressure changing device; and a cuff-pulse-wave detecting device which detects the cuff pulse wave occurring to the cuff.

* * * * *